(12) United States Patent
Melder et al.

(10) Patent No.: US 12,268,438 B2
(45) Date of Patent: Apr. 8, 2025

(54) SYSTEMS, DEVICES, AND METHODS FOR MODULATING RENAL NERVE TISSUE

(71) Applicant: Medtronic Ardian Luxembourg S.a.r.l., Luxembourg (LU)

(72) Inventors: Robert Melder, Santa Rosa, CA (US); Martin Rothman, Santa Rosa, CA (US); Stefan Tunev, Santa Rosa, CA (US)

(73) Assignee: MEDTRONIC IRELAND MANUFACTURING UNLIMITED COMPANY, Dublin (IE)

( * ) Notice: Subject to any disclaimer, the term of this patent is extended or adjusted under 35 U.S.C. 154(b) by 0 days.

(21) Appl. No.: 18/163,615

(22) Filed: Feb. 2, 2023

(65) Prior Publication Data
US 2023/0181251 A1 Jun. 15, 2023

Related U.S. Application Data

(63) Continuation of application No. 16/271,742, filed on Feb. 8, 2019, now abandoned, which is a continuation
(Continued)

(51) Int. Cl.
*A61B 18/14* (2006.01)
*A61B 18/00* (2006.01)
(Continued)

(52) U.S. Cl.
CPC .............. *A61B 18/1492* (2013.01); *A61B 2018/00214* (2013.01); *A61B 2018/00261* (2013.01);
(Continued)

(58) Field of Classification Search
CPC ........ A61B 18/1492; A61B 2018/00285; A61B 2018/1435; A61B 2018/1475
See application file for complete search history.

(56) References Cited

U.S. PATENT DOCUMENTS

| | | | |
|---|---|---|---|
| 2005/0288730 A1* | 12/2005 | Deem ................ | A61N 1/36017 607/42 |
| 2006/0235474 A1* | 10/2006 | Demarais ........... | A61N 1/36114 607/2 |

(Continued)

*Primary Examiner* — Rex R Holmes
*Assistant Examiner* — Jennifer L Ghand
(74) *Attorney, Agent, or Firm* — Shumaker & Sieffert, P.A.

(57) ABSTRACT

Methods for treating a patient using therapeutic renal neuromodulation and associated devices, system, and methods are disclosed herein. One aspect of the present technology is directed to neuromodulating nerve tissue in selected anatomical regions. In one embodiment, the method can include intravascularly advancing an elongate shaft of a catheter to renal vasculature of a human patient and locating a first neuromodulation element of the catheter within a distalmost portion of a main renal artery. The method includes locating a second neuromodulation element of the catheter within a branch vessel of the renal artery distal to a bifurcation at a distal end of the main renal artery. Neuromodulation of the nerve tissue surrounding the selected anatomical treatment locations can inhibit sympathetic neural activity in nerves proximate a portion of a renal artery and/or a renal branch artery proximate a renal parenchyma.

20 Claims, 21 Drawing Sheets

Related U.S. Application Data of application No. 14/713,604, filed on May 15, 2015, now abandoned.

(60) Provisional application No. 62/136,136, filed on Mar. 20, 2015, provisional application No. 62/103,460, filed on Jan. 14, 2015, provisional application No. 62/064,929, filed on Oct. 16, 2014, provisional application No. 62/049,058, filed on Sep. 11, 2014, provisional application No. 62/042,832, filed on Aug. 28, 2014, provisional application No. 61/994,595, filed on May 16, 2014, provisional application No. 61/994,744, filed on May 16, 2014.

(51) Int. Cl.
  *A61B 18/08* (2006.01)
  *A61B 18/18* (2006.01)
  *A61B 18/24* (2006.01)
  *A61N 7/02* (2006.01)

(52) U.S. Cl.
  CPC ............ *A61B 2018/00285* (2013.01); *A61B 2018/00404* (2013.01); *A61B 2018/00434* (2013.01); *A61B 2018/00511* (2013.01); *A61B 2018/00577* (2013.01); *A61B 18/082* (2013.01); *A61B 2018/1435* (2013.01); *A61B 2018/1475* (2013.01); *A61B 2018/1861* (2013.01); *A61B 18/24* (2013.01); *A61N 7/022* (2013.01)

(56) References Cited

U.S. PATENT DOCUMENTS

| | | | |
|---|---|---|---|
| 2007/0129720 A1* | 6/2007 | Demarais | A61N 1/36007 606/41 |
| 2012/0136350 A1* | 5/2012 | Goshgarian | A61B 18/1492 606/41 |
| 2013/0116737 A1* | 5/2013 | Edwards | A61B 5/4041 607/2 |
| 2013/0274614 A1* | 10/2013 | Shimada | A61B 5/0205 600/587 |
| 2013/0325000 A1* | 12/2013 | Bates | A61B 18/1492 606/41 |
| 2015/0245867 A1* | 9/2015 | Gross | A61B 18/1492 606/34 |
| 2016/0058503 A1* | 3/2016 | Tunev | A61B 18/1492 606/41 |

* cited by examiner

Renal Denervation Preclinical Efficacy:
Review of 66 Treated and 64 Naïve Swine

| Group Heartflow or Kidneys | 72 Hour Functional Area | Cortical Axon Area per mm² | Mean NE (pg/mg) |
|---|---|---|---|
| Naïve 7 day N=64 | 14.6 ± 8.0 | 207.2 ± 134.6 | 264.8 ± 82.9 |
| Symplicity 7 Day N=54 | 56.9 ± 28.3 | 66.8 ± 84.6 (68% Decrease) | 92.7 ± 92.7 (65% Decrease) |
| Spyral 7 Day N=12 | 47.3 ± 26.5 | 97.4 ± 73.1 (54% Decrease) | 88 ± 75 (68% Decrease) |

Fig. 16A

SYSTEMS, DEVICES, AND METHODS FOR MODULATING RENAL NERVE TISSUE

CROSS-REFERENCE TO RELATED APPLICATIONS

This application is a continuation of U.S. application Ser. No. 16/271,742, filed Feb. 8, 2019, which is a continuation of U.S. application Ser. No. 14/713,604, filed May 15, 2015, which claims the benefit of:

U.S. Provisional Patent Application No. 61/994,744, filed May 16, 2014;

U.S. Provisional Patent Application No. 62/042,832, filed Aug. 28, 2014;

U.S. Provisional Patent Application No. 62/049,058, filed Sep. 11, 2014;

U.S. Provisional Patent Application No. 62/064,929, filed Oct. 16, 2014;

U.S. Provisional Patent Application No. 62/103,460, filed Jan. 14, 2015;

U.S. Provisional Patent Application No. 61/994,595, filed May 16, 2014; and

U.S. Provisional Patent Application No. 62/136,136, filed Mar. 20, 2015.

All of the foregoing applications are incorporated herein by reference in their entireties. Further, components and features of embodiments disclosed in the applications incorporated by reference may be combined with various components and features disclosed and claimed in the present application.

TECHNICAL FIELD

The present technology is related to neuromodulation, such as renal neuromodulation and systems, devices, and methods for performing renal neuromodulation on human patients.

BACKGROUND

The sympathetic nervous system (SNS) is a primarily involuntary bodily control system typically associated with stress responses. Fibers of the SNS extend through tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS, in particular, has been identified experimentally and in humans as a likely contributor to the complex pathophysiologies of hypertension, states of volume overload (e.g., heart failure), and progressive renal disease.

Sympathetic nerves of the kidneys terminate in the renal blood vessels, the juxtaglomerular apparatus, and the renal tubules, among other structures. Stimulation of the renal sympathetic nerves can cause, for example, increased renin release, increased sodium reabsorption, and reduced renal blood flow. These and other neural-regulated components of renal function are considerably stimulated in disease states characterized by heightened sympathetic tone. For example, reduced renal blood flow and glomerular filtration rate as a result of renal sympathetic efferent stimulation is likely a cornerstone of the loss of renal function in cardio-renal syndrome. Pharmacologic strategies to mitigate adverse consequences of renal sympathetic stimulation often include the use of centrally-acting sympatholytic drugs, beta blockers, angiotensin-converting enzyme inhibitors, and/or diuretics. These and other pharmacologic strategies, however, tend to have significant limitations including limited efficacy, compliance issues, and undesirable side effects.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

As shown in FIG. 4, the first catheter can include a first shaft and a first neuromodulation element. The first neuromodulation element can include a first balloon. In FIG. 4, the first neuromodulation element is in an expanded treatment state within the distalmost portion of the main vessel.

As shown in FIG. 5, the second catheter can include a second shaft and a second neuromodulation element. The second neuromodulation element can include a second balloon. In FIG. 5, the second neuromodulation element is in a low-profile delivery state within a branch vessel of the renal vasculature.

In FIG. 6, the second neuromodulation element is in an expanded treatment state within the branch vessel.

As shown in FIG. 9, the first neuromodulation element is deployed from the sheath and in an expanded treatment state within the distalmost portion of the main vessel and the second neuromodulation element is deployed from the sheath and in its low-profile delivery state within the distalmost portion of the main vessel.

As shown in FIG. 10, the second neuromodulation element is deployed from the sheath and in its low-profile delivery state within the main vessel. The first neuromodulation element (not shown in FIG. 10) is also in its low-profile delivery state within the main vessel.

As shown in FIG. 11, the second neuromodulation element is deployed from the sheath and in its low-profile delivery state within a branch vessel. The first neuromodulation element (not shown in FIG. 11) is in its low-profile delivery state within the main vessel.

As shown in FIG. 12, the second neuromodulation element is in an expanded treatment state within the branch vessel. The first neuromodulation element (not shown in FIG. 12) is its low-profile delivery state within the main vessel.

FIG. 16A is a diagram illustrating results from a study to determine the effects of renal denervation on cortical axon density and mean norepinephrine concentration on animal subjects.

DETAILED DESCRIPTION

The present technology is related to neuromodulation, such as renal neuromodulation, and systems, devices, and methods for performing renal neuromodulation on human patients. The inventors have discovered, among other things, that targeting certain locations within a patient's renal vasculature may increase the efficacy of renal neuromodulation for achieving one or more desired clinical outcomes, such as lowering of a patient's blood pressure. Renal neuromodulation treatments can include, for example, targeting one or more anatomical regions of the patient's renal vasculature, and can include a combination of treating one or more proximal and/or central portions of the main artery, one or more distal portions of the main artery, one or more branch vessels, and/or at one or more bifurcations of the renal vasculature. A renal neuromodulation method in accordance with a particular embodiment of the present technology includes preferentially targeting nerve tissue for treatment within an anatomical region extending circumferentially around a distalmost portion (e.g., a distalmost third, quarter, or other suitable fraction) of a main vessel of a patient's renal vasculature. In addition or alternatively, the method can include preferentially targeting nerve tissue for treatment within an anatomical region extending circumferentially around one or more branch vessels of a patient's renal vasculature. In further embodiments, the method can include targeting nerve tissue within an anatomical region extending circumferentially around one or more branch vessels and around one or more portions (e.g., a proximal portion, a central portion, a distalmost portion) of the main vessel of a patient's renal vasculature. Targeting nerve tissue for treatment within these anatomical regions may allow a neuromodulation procedure to reliably achieve relatively comprehensive renal neuromodulation, i.e., adequately treating all or nearly all of these nerve fibers innervating a kidney.

Figure 1:
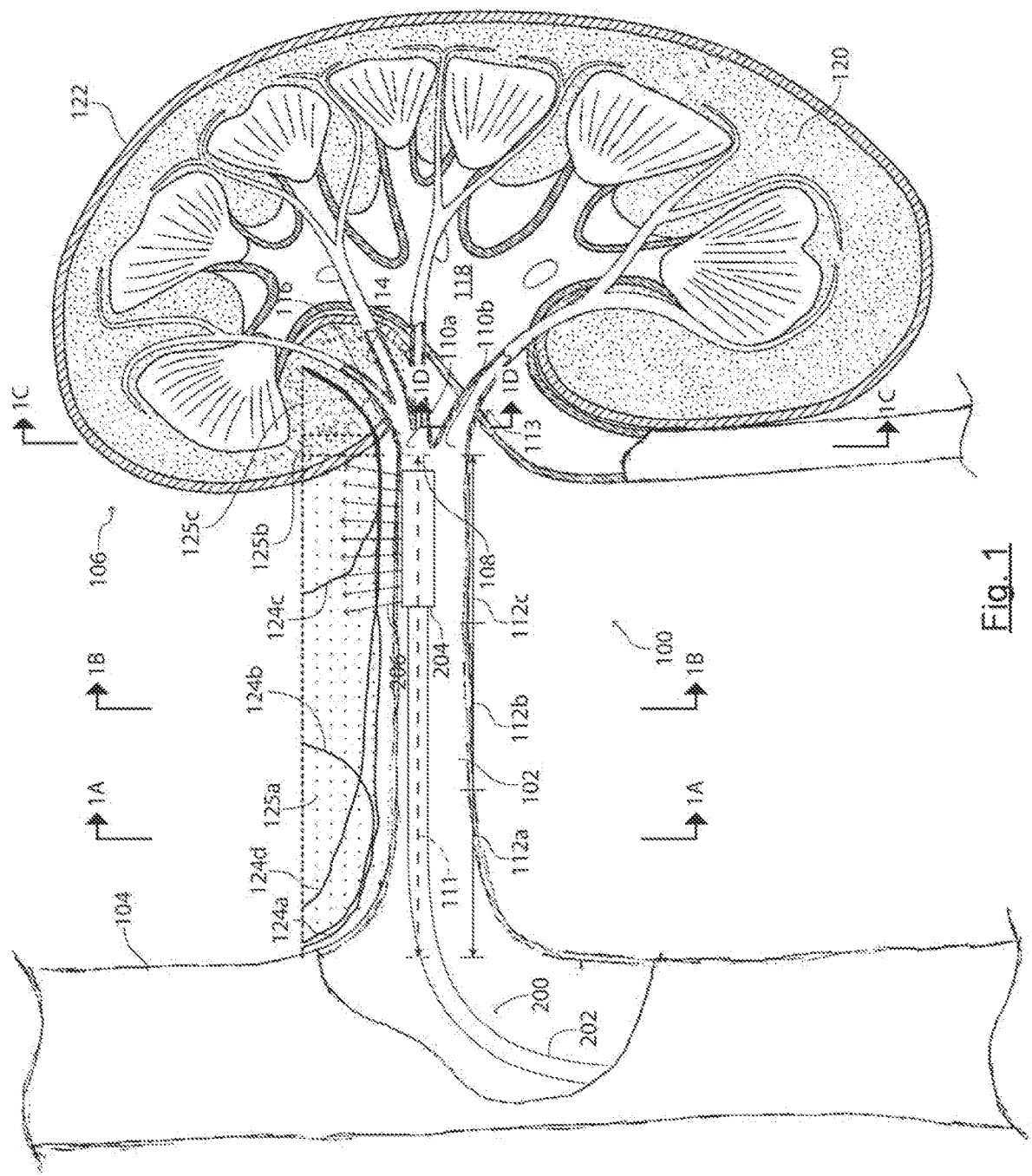
FIG. 1 is a partially cross-sectional profile view illustrating a neuromodulation element (shown schematically) of a catheter delivering energy to nerve tissue within an anatomical region extending circumferentially around a distalmost portion of a main vessel of renal vasculature of a human patient in accordance with an embodiment of the present technology.
Figure 2:
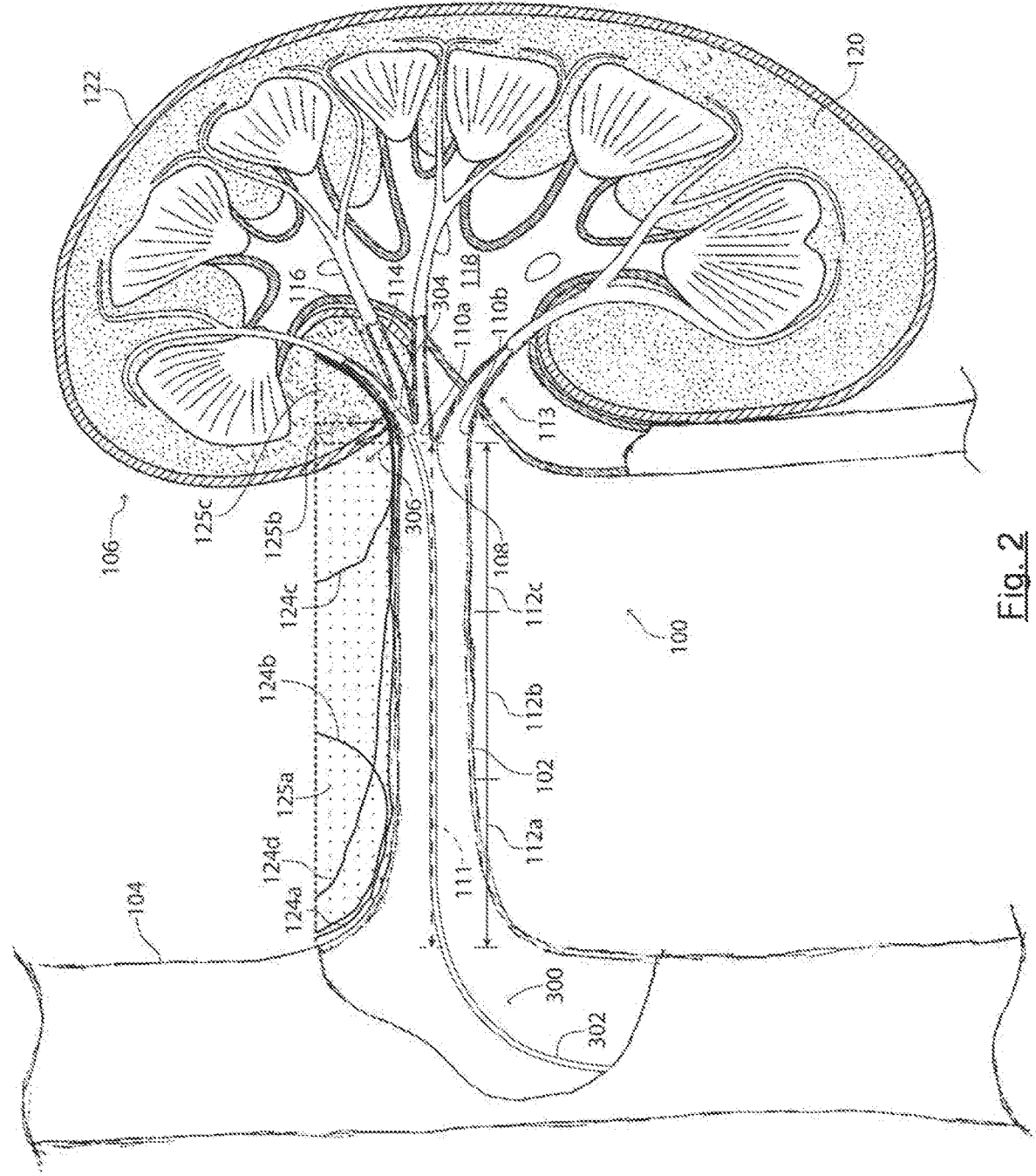
FIG. 2 is a partially cross-sectional profile view illustrating a neuromodulation element (shown schematically) of a catheter delivering energy to nerve tissue within an anatomical region extending circumferentially around a portion of a branch vessel of the renal vasculature in accordance with an embodiment of the present technology.

FIGS. 1 and 2 are partially cross-sectional profile views illustrating neuromodulation methods in accordance with embodiments of the present technology. FIGS. 1 and 2 also illustrate renal vasculature 100 of a human patient and associated anatomy. The renal vasculature 100 includes a main vessel 102 (e.g., a main artery) directly connected to an aorta 104 and extending distally toward a kidney 106. The renal vasculature 100 further includes a primary bifurcation 108 at a distal end of the main vessel 102, a first primary branch vessel 110a extending distally from the main vessel 102 beginning at the primary bifurcation 108, and a second primary branch vessel 110b extending distally from the main vessel 102 also beginning at the primary bifurcation 108. The main vessel 102 has a longitudinal axis 111 and a corresponding length 112 extending distally from the aorta 104 to the primary bifurcation 108. Distal to the first and second primary branch vessels 110a, 110b, the renal vasculature 100 includes a network 113 of subordinate branch vessels 114 and subordinate bifurcations 116. For clarity of illustration only one subordinate branch vessel 114 and one subordinate bifurcation 116 are identified in FIGS. 1 and 2. From the subordinate branch vessels 114, the network 113 branches into capillaries (not shown) that supply blood to the kidney 106. The first and second primary branch vessels 110a, 110b can be, for example, segmental arteries. The subordinate branch vessels 114 can be, for example, segmental arteries, interlobular arteries, and/or arcuate arteries. Collectively, the first primary branch vessel 110a, the second primary branch vessel 110b, and the subordinate branch vessels 114 are referred to herein as the branch vessels 110a, 110b, 114.

In human patients, the main vessel 102 (main renal artery) generally has a diameter of 6.27+/−1.27 mm. The primary branch vessels 110a/110b generally have diameters of 2.86+/−0.84 mm. As noted above, subordinate branch vessels 114 may include segmental arteries (with diameters of 1.94+/−0.68 mm), interlobular arteries (diameters of 0.90+/−0.22 mm), and/or arcuate arteries (diameters of 0.30+/−0.19 mm).

The kidney 106 includes a pelvis 118 and a cortex 120 extending around the pelvis 118. Blood flows into the kidney 106 through arteries of the renal vasculature 100 via the pelvis 118 and flow out of the kidney 106 through veins (not shown) of the renal vasculature 100 also via the pelvis 118. The kidney 106 further includes a capsule 122 encasing the cortex 120. The capsule 122 may preclude passage of nerve tissue. Thus, all or substantially all renal neural communication follows the renal artery and flows into and out of the kidney 106 through the renal pelvis 118. Several examples of nerve fibers 124 are shown in FIGS. 1 and 2. For clarity of illustration, the nerve fibers 124 are shown in FIGS. 1 and 2 in two dimensions and extending through a first anatomical region 125a adjacent to the main vessel 102, a second anatomical region 125b adjacent to the first primary branch vessel 110a, and a third anatomical region 125c adjacent to one of the subordinate branch vessels 114. Also for clarity of illustration, the nerve fibers 124 are shown as single fibers; however, it is understood that nerves are typically arranged in nerve bundles each having more than one nerve fiber along the first, second and third anatomical regions 125a-c. It should be understood that the first, second, and third anatomical regions 125a-125c extend circumferentially in three dimensions around the main vessel 102, the first primary branch vessel 110a, and the subordinate branch vessel 114, respectively. It should also be understood that the anatomy associated with the renal vasculature 100 includes other anatomical regions extending circumferentially in three dimensions around the second primary branch vessel 110b and additional subordinate branch vessels 114, respectively, and that the nerve fibers 124 can be distributed at various locations in three dimensions within the first, second, and third anatomical regions 125a-125c and within these other anatomical regions. Collectively, the first, second, and third anatomical regions 125a-125c and these other anatomical regions are identified herein as the anatomical regions 125. As shown in FIGS. 1 and 2, the anatomical regions 125 can include tissue outside the capsule 122 as well as tissue inside the capsule 122.

The nerve fibers 124 bifurcate at or near the primary and subordinate bifurcations 108, 116 and follow the subordinate branch vessels 114 fairly closely within the cortex 120. The nerve fibers 124 eventually terminate at various levels of the renal arterial tree up to and including the afferent arterioles where they can control vasodilation and vasoconstriction. In some cases, all of the nerve fibers 124 also follow the main vessel 102 fairly closely within a well-defined plexus and extend along the entire length 112 of the main vessel 102 or nearly the entire length 112 of the main vessel 102 at a relatively uniform distance from a wall of the main vessel 102. In these cases, a neuromodulation treatment at any portion of the first anatomical region 125a is expected to be efficacious.

By way of theory (and without wishing to be bound by theory), in certain other cases only some of the nerve fibers 124 (e.g., the nerve fiber 124a) are of a first type that extends along the entire length 112 of the main vessel 102 or nearly the entire length 112 of the main vessel 102 at a relatively uniform distance from a wall of the main vessel 102. As mentioned above, a renal neuromodulation treatment performed at any position along the length 112 of the main vessel 102 may be relatively effective for treating this first type of nerve fiber 124. Other nerve fibers 124 (e.g., the nerve fiber 124b), however, may be of a second type extending along a proximal part of the length 112 of the main vessel 102 and then diverging from the main vessel 102 toward a non-renal destination. Further, other nerve fibers 124 (e.g., the nerve fiber 124c) may be of a third type that approaches the wall of the main vessel 102 abruptly at a relatively distal position along the length 112 of the main vessel 102. Still further, other nerve fibers 124 (e.g., the nerve fiber 124d) may be of a fourth type that approaches the wall of the main vessel 102 gradually along the length 112 of the main vessel 102 from proximal to distal. Other types of nerve fibers 124 are also possible.

Renal neuromodulation treatments performed at certain positions along the length 112 of the main vessel 102 may have advantages relative to renal neuromodulation procedures performed at other positions along the length 112 of the main vessel 102. For example, a renal neuromodulation treatment performed from within the main vessel 102 at a relatively distal position along the length 112 of the main vessel 102 and/or from within one or more of the branch vessels 110a, 110b, 114 may avoid treating the second type of nerve fibers 124 (e.g., the nerve fiber 124b) unnecessarily. This can be useful, for example, because nerve fibers 124 of the second type do not terminate within the kidney 106. As another example, a renal neuromodulation treatment performed from within the main vessel 102 at a relatively distal position along the length 112 of the main vessel 102 and/or from within one or more of the branch vessels 110a, 110b, 114 may be well-suited for treating the third type of nerve fibers 124 (e.g., the nerve fiber 124c), such as by delivering energy distal to where the nerve fibers 124 join the path of the main vessel 102.

Figure 1A:
FIGS. 1A-1D are cross-sectional histological images taken from human cadavers and showing the proximity of the nerve fibers 124 along portions of the renal vasculature shown in FIG. 1.
Figure 1B:
Figure 1C:
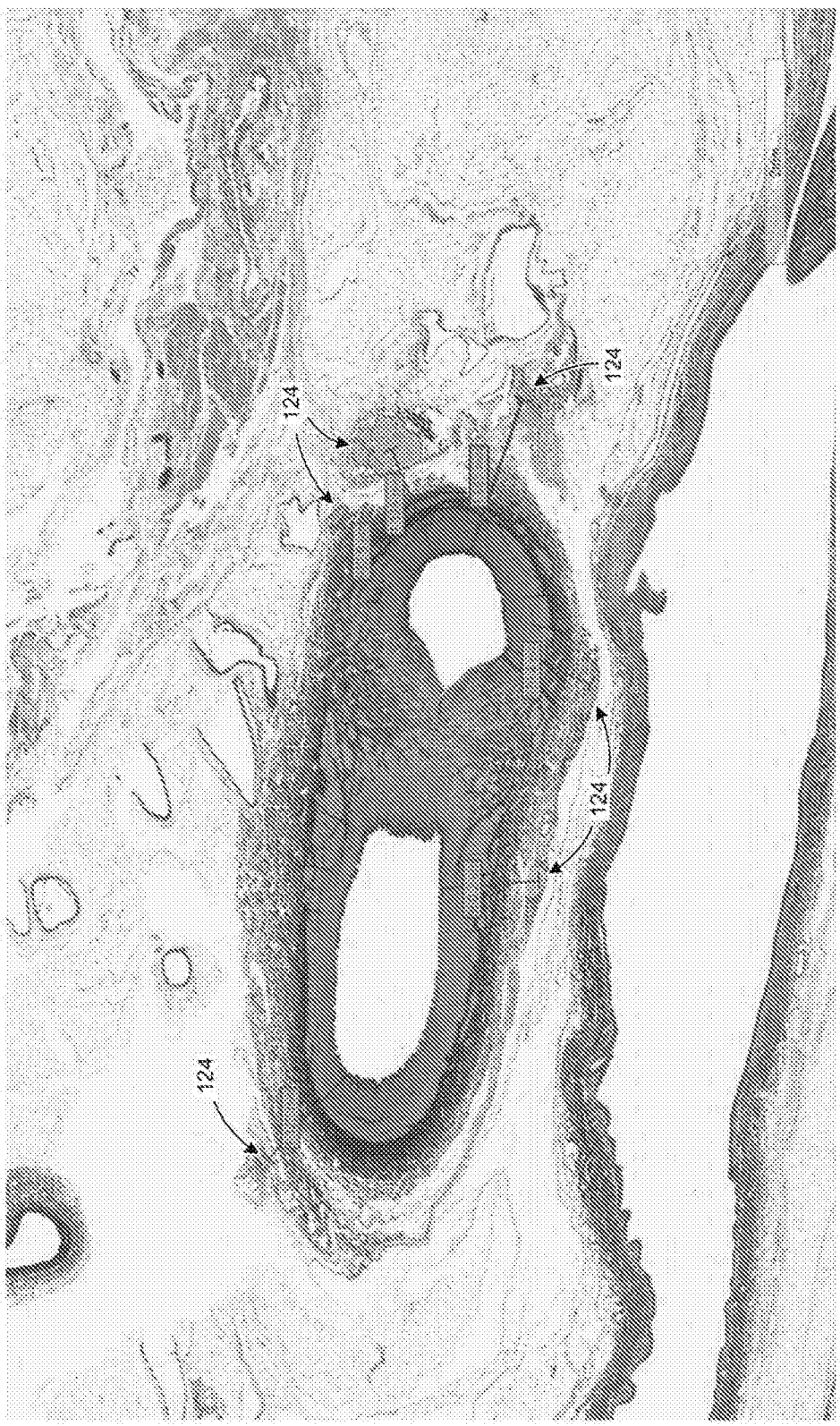
Figure 1D:
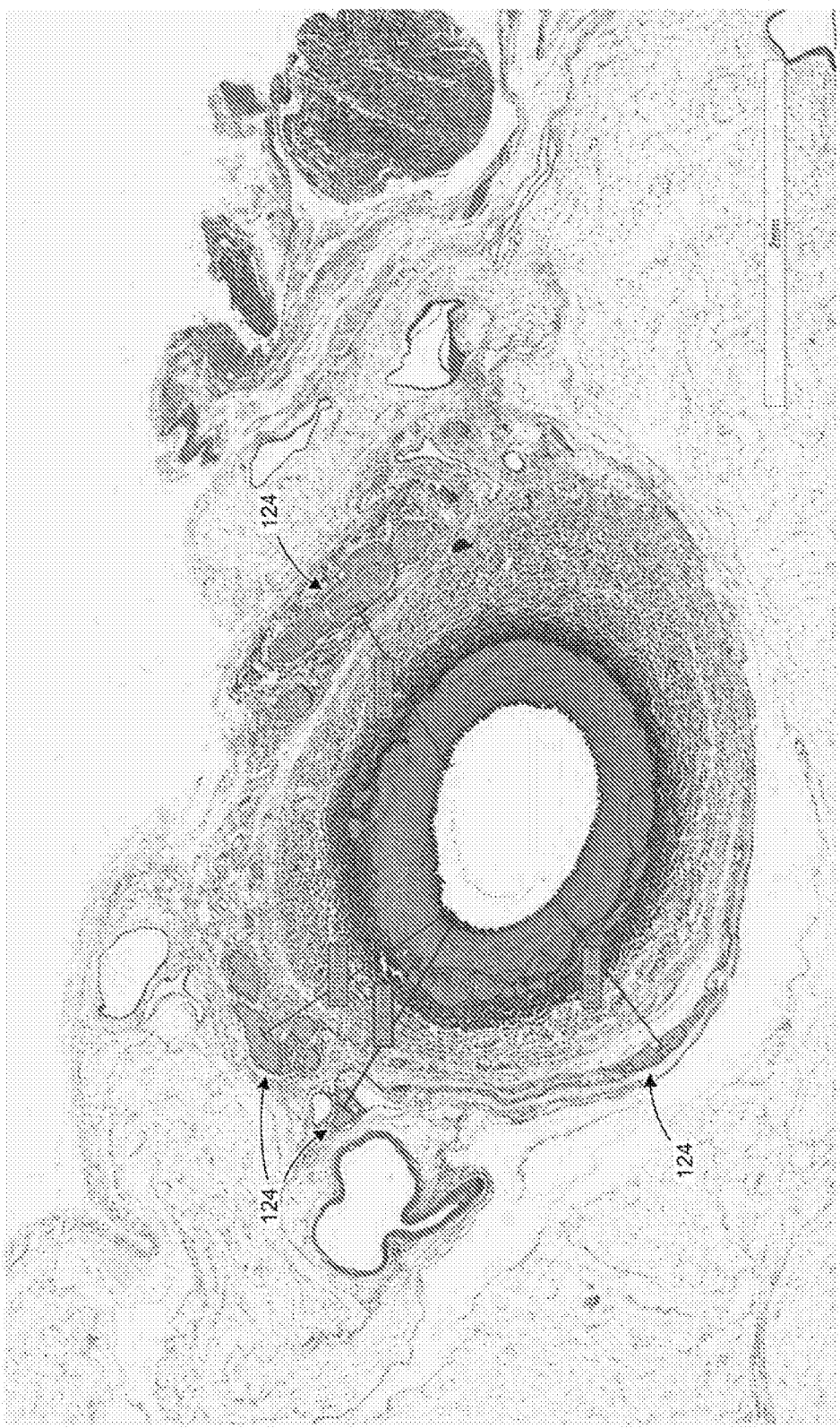

As yet another example, a renal neuromodulation treatment performed from within the main vessel 102 at a relatively distal position along the length 112 of the main vessel 102 and/or from within one or more of the branch vessels 110a, 110b, 114 may be well-suited for providing a therapeutically effective amount of energy to the fourth type of nerve fibers 124 (e.g., the nerve fiber 124d), such as by delivering energy distal to a point along the length 112 of the main vessel 102 at which the nerve fibers 124 begin to travel along the length 112 of the main vessel 102 in close enough proximity to a wall of the main vessel 102 to be within a therapeutically effective range of a neuromodulation element. For example, in portions of the renal vasculature, a greater number of nerve fibers 124 are accessible (e.g., within range) to the neuromodulating treatment. FIGS. 1A-1D are cross-sectional histological images showing the proximity of the nerve fibers 124 along portions of the renal vasculature shown in FIG. 1. FIG. 1A shows the proximity of nerve fibers 124 to an inner wall of the proximal portion of the main renal artery and FIG. 1B shows the proximity of nerve fibers 124 to the inner wall of the central/middle portion of the main renal artery. FIG. 1C shows the proximity of nerve fibers 124 to an inner wall of branch vessels at the bifurcation of the main renal artery and FIG. 1D shows the proximity of nerve fibers 124 to an inner wall of a branch vessel distal to the bifurcation. Referring to FIGS. 1A-1D together, the nerve fibers 124 are shown to be closer in proximity (e.g., more accessible to treatment originating from the inner lumen of the renal arterial vasculature) at the bifurcation and branch vessels as compared to the proximal and central/middle portions of the main renal artery. Accordingly, systems, devices, and methods for performing renal neuromodulation in accordance with embodiments of the present technology are expected to be well-suited for effectively treating the first, third, and fourth types of nerve fibers 124, while avoiding unnecessary treatment of the second type of nerve fibers 124.

In a further example, the therapeutic energy (e.g., radiofrequency (RF) energy) can be delivered at different levels (e.g., intensities, power levels) at varying positions along the length 112 of the main vessel 102 and/or the branches. For example, in regions of the renal vasculature where the nerve fibers 124 are further from the inner wall of the vessel, the power may be increased. By increasing the power output from the electrode, the RF energy can increase the three-dimensional area of the resulting lesion. As such, the resultant larger lesion would reach greater tissue depths from the inner wall of the vessel. Likewise, where the nerve fibers 124 are found closer to the inner wall of the vessel, the power may be selectively decreased such that damage to non-target tissue is minimized while still achieving successful denervation. In some embodiments, the system (e.g., console 1402, discussed further with respect to FIG. 13 below) and/or electrodes spaced apart along a multi-electrode neuromodulation element, can be configured such that the electrodes individually supply different and/or varying amounts of energy (e.g., RF energy) based on the electrode's location along the vasculature. For example, the system can be configured such that an electrode positioned along the proximal portion of the main vessel 102 imparts higher power than an electrode positioned along the distalmost portion of the main vessel 102 and/or the branch vessels 110a, 110b, 114.

In further embodiments, the system and/or electrode(s) can be configured to vary the duration of power delivery either collectively or individually (e.g., in embodiments having multi-electrode neuromodulation elements). In various arrangements, the duration of power delivery can vary depending on the position of one or more electrodes along the vasculature. For example, the system can be configured such that an electrode positioned along the proximal portion of the main vessel 102 imparts power for a longer duration than an electrode positioned along the distalmost portion of the main vessel 102 and/or the branch vessels 110a, 110b, 114. In a particular embodiment, for example, the electrodes spaced apart along a multi-electrode neuromodulation element can be controlled to selectively deliver power at individually selected power levels and for individually selected durations such that power delivery is optimized for targeting nerve tissue at varying depths along the renal vasculature.

In yet further embodiments, the electrodes in a multi-electrode neuromodulation element can be configured to be optionally and selectively deactivated (e.g., in some instances in which a branch vessel 110a, 110b, 114 is short, narrow, or otherwise undesirable for treatment). In various arrangements, the deselection of electrodes can vary depending upon the relative position of the individual electrodes along the branch vasculature. For example, the multi-electrode neuromodulation element can be inserted in a branch vessel such that the proximal-most electrode is distal to the primary bifurcation (e.g., approximately 1 mm-5 mm distal to the primary bifurcation, approximately 2 mm-6 mm distal to the primary bifurcation, approximately 5 mm distal to the primary bifurcation, etc.). In this example, and in instances in which the branch vessel is short, narrow, or otherwise undesirable for treatment (e.g., tortuous, stenosed, etc.), one or more distalmost electrodes can be optionally and selectively deactivated. In another example, the multi-electrode neuromodulation element can be inserted into a branch vessel such that a proximal portion of the multi-electrode element can be close to or span across the first bifurcation. In such embodiments, one or more of the proximal electrodes can be optionally and selectively deactivated such that the electrodes at or near the bifurcation do not receive energy (e.g., RF energy) while the distalmost electrodes deliver energy to the vessel wall for performing ablations. In a further example, electrode(s) positioned between the distalmost and proximal-most electrodes (e.g., intermediate electrode(s)) can be deselected, for example, if sufficient or stable wall contact is prevented or undesirable because of patient-specific anatomical features (e.g., tortuous vessel, stenosed vessel, etc.).

In further examples, renal neuromodulation treatments can be performed at certain positions along the length 112 of the main vessel 102, the branch vessels 110a, 110b, 114, or both in a patient-specific dependent manner. For example, a clinician can assess via angiogram, fluoroscope, etc., a patient's particular anatomy and disease state (e.g., stenosis, arthrosclerosis, vessel diameter, degree of vessel torsion, vessel length, branch length distal to the bifurcation, etc.) and determine one or more desirable locations for renal neuromodulation treatment.

The main vessel 102 may be stented or unstented during renal neuromodulation in accordance with at least some embodiments of the present technology. In one example, the main vessel 102 is stented in an earlier attempt to achieve a desired clinical outcome. Renal neuromodulation in accordance with an embodiment of the present technology may be used when stenting the main vessel 102 is not effective or is insufficiently effective for achieving the clinical outcome. For example, renal neuromodulation in accordance with an embodiment of the present technology may be used to supplement the therapeutic effect, if any, of stenting the main vessel 102 on lowering a patient's blood pressure. Alternatively or in addition, stenting the main vessel 102 and renal neuromodulation in accordance with an embodiment of the present technology may have different purposes. Typically, when present, a renal stent (not shown) is located at a proximal portion of the main vessel 102. From this position, the stent is unlikely to interfere with the methods illustrated in FIGS. 1 and 2. Thus, these methods and at least some other methods in accordance embodiments of the present technology may be more compatible with a stented main vessel 102 than at least some conventional counterparts.

Specific details of systems, devices, and methods in accordance with several embodiments of the present technology are disclosed herein with reference to FIGS. 1-15B. Although the systems, devices, and methods may be disclosed herein primarily or entirely with respect to intra-arterial renal neuromodulation, other applications in addition to those disclosed herein are within the scope of the present technology. For example, systems, devices, and methods in accordance with at least some embodiments of the present technology may be useful for neuromodulation within one or more non-arterial or non-vessel body lumens, for extravascular neuromodulation, for non-renal neuromodulation, and/or for use in therapies other than neuromodulation. Furthermore, it should be understood, in general, that other systems, devices, and methods in addition to those disclosed herein are within the scope of the present technology. For example, systems, devices, and methods in accordance with embodiments of the present technology can have different and/or additional configurations, components, and procedures than those disclosed herein. Moreover, a person of ordinary skill in the art will understand that systems, devices, and methods in accordance with embodiments of the present technology can be without one or more of the configurations, components, and/or procedures disclosed herein without necessarily deviating from the present technology.

Selected Examples of Neuromodulation Methods and Associated Technology

As shown in FIG. 1, a catheter 200 including an elongate shaft 202 and a neuromodulation element 204 (shown schematically) operably connected to the shaft 202 can be located such that the neuromodulation element 204 is distally positioned along the length 112 of the main vessel 102. In the illustrated embodiment, for example, the neuromodulation element 204 is located at least predominantly within a distal portion of the main vessel 102. Portions of the length 112 of the main vessel 102 corresponding to a distalmost third 112a, a middle third 112b, and a proximal-most third 112c of the main vessel 102 are respectively indicated in FIGS. 1 and 2.

As shown in FIG. 2, a catheter 300 including an elongate shaft 302 and a neuromodulation element 304 (shown schematically) operably connected to the shaft 302 can be located such that the neuromodulation element 304 is within the first primary branch vessel 110a. In the illustrated embodiment, the neuromodulation element 304 partially extends into one of the subordinate branch vessels 114. In other embodiments, however, the neuromodulation element 304 can be entirely within the first primary branch vessel 110a or partially extended into more than one of the subordinate branch vessels 114 and/or into the main vessel 102.

With reference to FIGS. 1 and 2 together, the neuromodulation elements 204, 304 can be more longitudinally compact than at least some conventional counterparts and can be positioned at respective treatment sites within the renal vasculature 100 relatively well-suited for comprehensively treating the nerve fibers 124. From its position shown in FIG. 1, the neuromodulation element 204 can be used to deliver energy (represented by arrows 206) to the nerve fibers 124 within a portion of the first anatomical region 125a extending around the distal portion of the main vessel 102. From its position shown in FIG. 2, the neuromodulation element 304 can be used to deliver energy (represented by arrows 306) to the nerve fibers 124 within a portion of the second anatomical region 125b extending around the first primary branch vessel 110a and within a portion of the third anatomical region 125c extending around one of the subordinate branch vessels 114. Typically, all or substantially all nerve fibers 124 targeted for treatment (e.g. nerve fibers 124 of the first, third, and fourth types discussed above, among others) are reliably found in close proximity to the renal vasculature 100 within the anatomical region 125 immediately distal and proximal to the primary bifurcation 108.

In FIG. 1, energy from the neuromodulation element 204 is shown extending in one planar direction toward the first anatomical region 125a. Similarly, in FIG. 2, energy from the neuromodulation element 304 is shown extending in one planar direction toward the second anatomical region 125b. These are simplified representations merely for clarity of illustration. Instead of extending in one planar direction, energy from the neuromodulation element 204 generally extends in many planar directions radially distributed about the longitudinal axis 111 of the main vessel 102. Similarly, energy from the neuromodulation element 304 generally extends in many planar directions radially distributed about a longitudinal axis (not shown) of the first primary branch vessel 110a.

In some embodiments, it may be desirable to avoid delivering energy in a pattern that causes a circumferentially continuous lesion to form within any plane perpendicular to the longitudinal axis 111 of the main vessel 102 or a longitudinal axis of any of the branch vessels 110a, 110b, 114. Such a lesion is thought to potentially increase the risk of stenosis. For this and/or other reasons relating to vessel wall preservation, it may be desirable to deliver energy to the anatomical regions 125 in a helical/spiral pattern. Beyond the wall of a vessel from which the energy is delivered, different portions of a lesion formed in this manner may expand toward one another while still remaining circumferentially discontinuous within any plane perpendicular to the longitudinal axis of the vessel. If the nerve fibers 124 extend parallel to the longitudinal axis of the vessel and the sum of different portions of the lesion along the longitudinal axis of the vessel extends around the entire circumference of the vessel, then such a lesion is expected to reach all or substantially all of the nerve fibers 124. In some cases, however, the nerve fibers 124 may not extend parallel to the longitudinal axis of the vessel. Instead, the individual nerve fibers 124 may be arborized, interwoven, or otherwise irregular in their respective paths through the anatomical regions 125. Accordingly, when a helical/spiral lesion extends over a relatively large portion of the length of the vessel, some of the nerve fibers 124 may follow paths that avoid contact with any part of the lesion. Accordingly, the neuromodulation elements 204, 304 can be configured to form more longitudinally compact lesions than those formed by at least some conventional neuromodulation elements.

Figure 3:
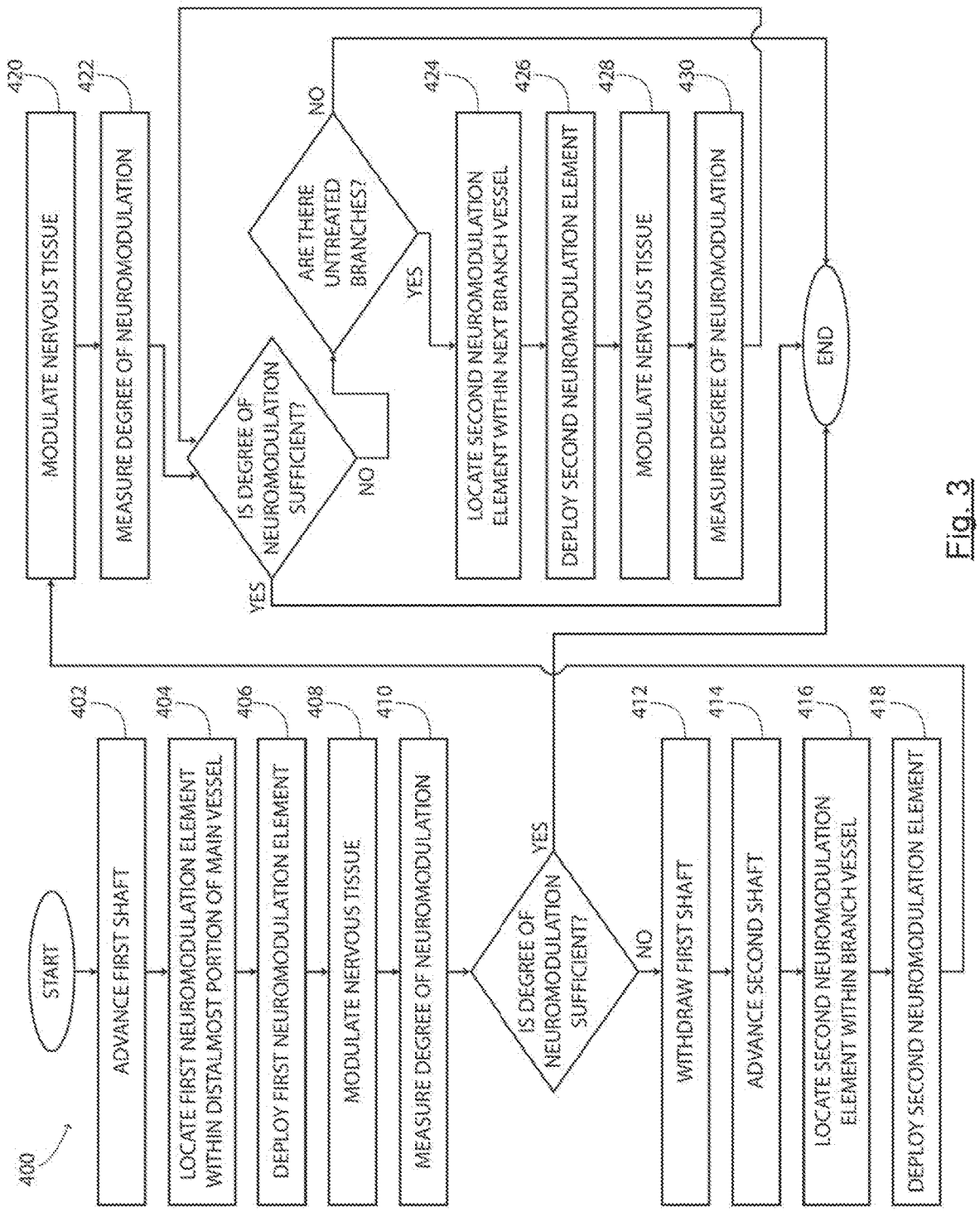
FIG. 3 is a flow chart illustrating a renal neuromodulation method in accordance with an embodiment of the present technology.
Figure 4:
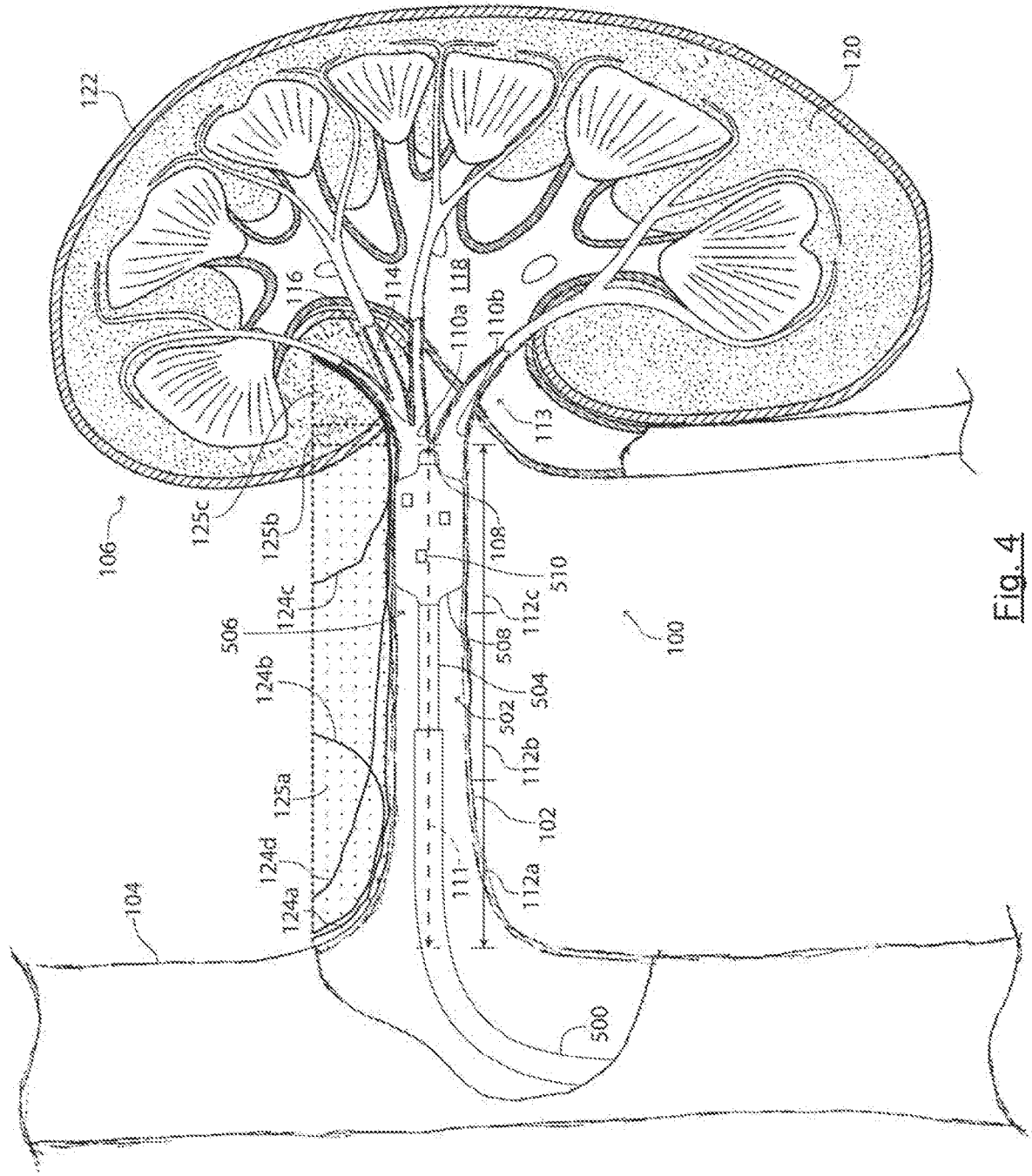
FIG. 4 is a partially cross-sectional profile view illustrating a first sheath and a first catheter within the renal vasculature in accordance with an embodiment of the present technology.
Figure 5:
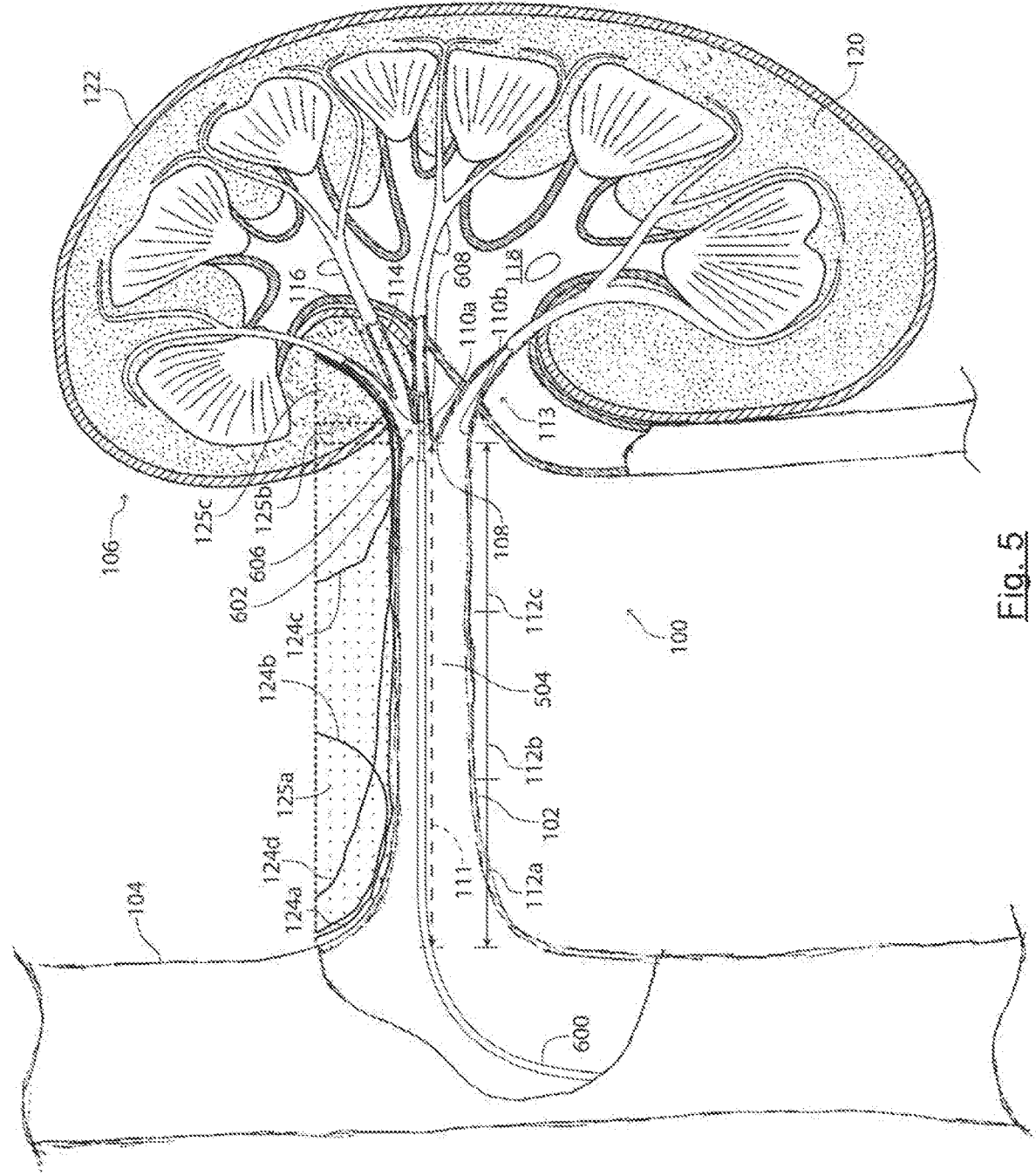
FIG. 5 is a partially cross-sectional profile view illustrating a second sheath and a second catheter within the renal vasculature in accordance with an embodiment of the present technology.
Figure 6:
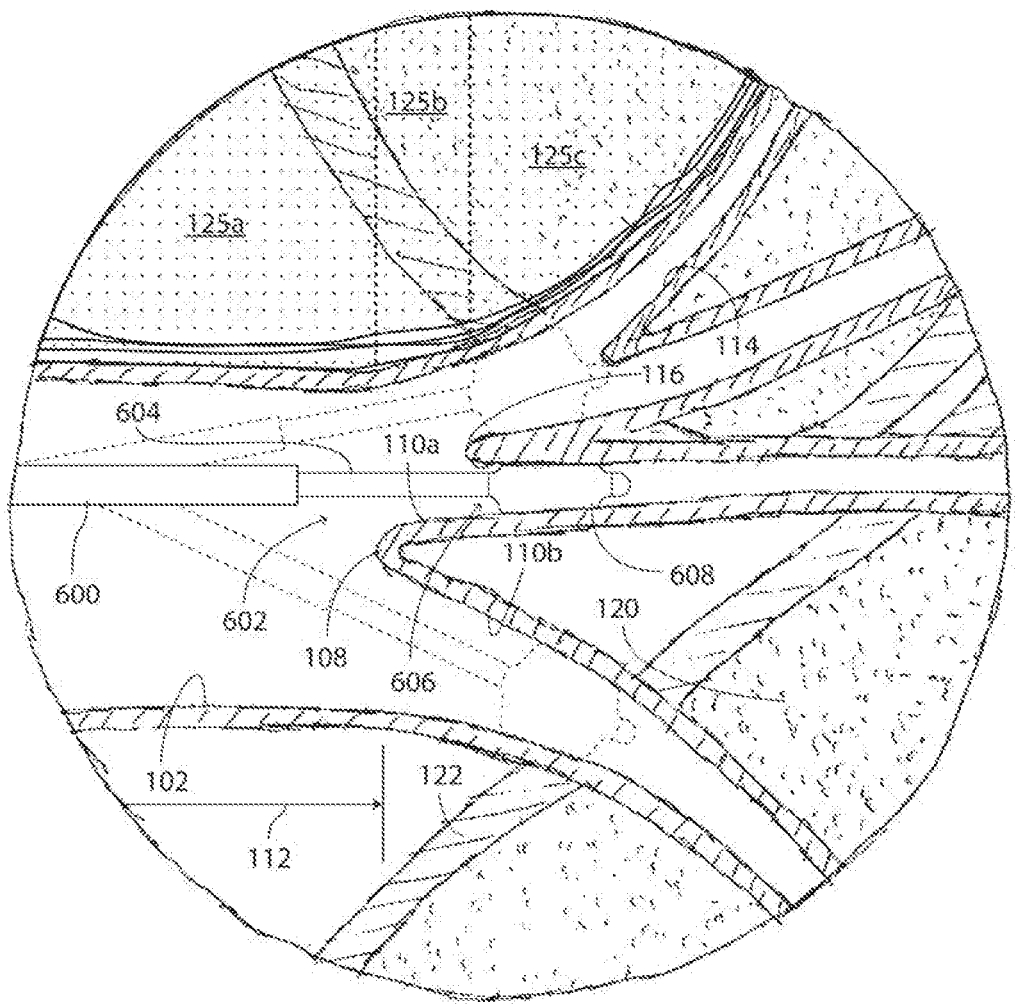
FIG. 6 is an enlarged, partially cross-sectional profile view illustrating the second sheath and the second catheter of FIG. 5 within the renal vasculature.

FIG. 3 is a flow chart illustrating a renal neuromodulation method 400 in accordance with an embodiment of the present technology. FIG. 4 is a partially cross-sectional profile view illustrating a first sheath 500 and a first catheter 502 within the renal vasculature 100 at one point during the method 400. As shown in FIG. 4, the first catheter 502 can include an elongate first shaft 504 and a first neuromodulation element 506 operably connected to the first shaft 504. FIG. 5 is a partially cross-sectional profile view illustrating a second sheath 600 and a second catheter 602 within the renal vasculature 100 at another point during the method 400. As shown in FIG. 5, the second catheter 602 can include an elongate second shaft 604 and a second neuromodulation element 606 operably connected to the second shaft 604. FIG. 6 is an enlarged, partially cross-sectional profile view illustrating the second sheath 600 and the second catheter 602 within the renal vasculature 100 at yet another point during the method 400.

With reference to FIGS. 3-6 together, the method 400 includes advancing the first shaft 504 intravascularly toward the renal vasculature 100, such as via a femoral, trans-radial or another suitable approach (block 402). While the first shaft 504 is advanced toward the renal vasculature 100, the first neuromodulation element 506 can be in a low-profile delivery state (not shown). For example, the first neuromodulation element 506 can include a first balloon 508, and the first balloon 508 can be deflated or otherwise unexpanded when the first neuromodulation element 506 is in the low-profile delivery state. After advancing the first shaft 504, the method 400 includes locating the first neuromodulation element 506 within the distal portion of the main vessel 102 (block 404). At this point, as shown in FIG. 4, the method 400 includes deploying the first neuromodulation element 506 into an expanded treatment state (block 406), such as by inflating or otherwise expanding the first balloon 508. The first neuromodulation element 506 can include first energy-delivery elements 510 (e.g., electrodes or transducers) spaced apart from one another and arranged in a helical/spiral pattern on an outside surface of the first balloon 508. As the first neuromodulation element 506 is deployed into the expanded treatment state, the first energy-delivery elements 510 move into contact with an inner surface of a wall of the main vessel 102.

Once the first neuromodulation element 506 is located within the distal portion of the main vessel 102 and in the expanded treatment state, the method 400 includes using the first neuromodulation element 506 to modulate nerve tissue within a portion of the first anatomical region 125a extending circumferentially around the distal portion of the main vessel 102 (block 408). The distal portion of the main vessel 102 can be, for example, a distalmost third of the main vessel 102, a distalmost quarter of the main vessel 102, a distalmost centimeter of the main vessel 102, or another suitable relatively distal portion of the main vessel 102. Modulating nerve tissue within the portion of the first anatomical region 125a extending circumferentially around the distal portion of the main vessel 102 can include, for example, preferentially modulating this nerve tissue relative to nerve tissue within portions of the first anatomical region 125a extending circumferentially around a proximal portion (e.g., a proximal-most third) and a middle portion (e.g., a middle third) of the main vessel 102. While some energy may be delivered to proximal or middle portions of the first anatomical region 125a, at least in the illustrated embodiment, the bulk of the energy released from the first neuromodulation element 506 is delivered to the distal portion of the first anatomical region 125a.

In at least some cases, the first neuromodulation element 506 is more longitudinally compact than conventional counterparts. For example, the first neuromodulation element 506 can be configured to form one or more lesions that extend through a wall of the main vessel 102 into the first anatomical region 125a along a helical/spiral path with relatively little distance (e.g., less than 4 millimeters on average) between neighboring turns. Once formed, the one or more lesions can be circumferentially continuous within the first anatomical region 125a along a plane perpendicular to a portion of the longitudinal axis 111 of the main vessel 102. The lesion(s) may extend through the distal portion of the main vessel 102 while still being circumferentially discontinuous at the wall of the main vessel 102 along all planes perpendicular to this portion of the longitudinal axis 111. This is expected to reduce or eliminate the possibility of the one or more lesions missing arborized nerve fibers 124 without causing undue risk of stenosis within the main vessel 102.

After using the first neuromodulation element 506, the method 400 includes measuring a first degree of neuromodulation achieved by using the first neuromodulation element 506 (block 410). Techniques for measuring the first degree of neuromodulation include measuring biomarkers, as further described in International Patent Application No. PCT/US2013/030041 (published as International Publication No. WO2013/134733 and titled "Biomarker Sampling in the Context of Neuromodulation Devices and Associated Systems and Methods") or inoperatively monitoring nerve activity, as further described in International Patent Application No. PCT/IB2012/003055 and titled "Endovascular Nerve Monitoring Devices and Associated Systems and Methods", both of which are incorporated herein by reference in their entireties. If the first degree of neuromodulation is sufficient (e.g., if the kidney 106 is at least substantially denervated), the method 400 can end. If the first degree of neuromodulation is not sufficient (e.g., if the kidney 106 is not at least substantially denervated), the method 400 includes withdrawing the first shaft 504 (block 412) and advancing the second shaft 604 intravascularly toward the renal vasculature 100 (block 414), such as along a guide wire or a guide lumen (not shown) also used to advance the first shaft 504 toward the renal vasculature 100.

As shown in FIG. 5, while the second shaft 604 is advanced toward the renal vasculature 100, the second neuromodulation element 606 can be in a low-profile delivery state. For example, the second neuromodulation element 606 can include a second balloon 608, and the second balloon 608 can be deflated or otherwise unexpanded when the second neuromodulation element 606 is in the low-profile delivery state. After advancing the second shaft 604, the method 400 includes locating the second neuromodulation element 606 within one of the branch vessels 110a, 110b, 114 distal to the primary bifurcation 108 (block 416). As discussed above, the second neuromodulation element 606 can also extend partially into one or more other vessels within the renal vasculature 100. In at least some cases, it can be useful to avoid positioning the second neuromodulation element 606 in direct contact with the primary bifurcation 108 so as to reduce the likelihood that the primary bifurcation 108 will be damaged during energy delivery. In some embodiments, such damage may contribute to stenosis.

At this point, as shown in FIG. 6, the method 400 can include deploying the second neuromodulation element 606 into an expanded treatment state (block 418), such as by inflating or otherwise expanding the second balloon 608. The second balloon 608 can carry one or more second energy-delivery elements (not shown) (e.g., electrodes or transducers) arranged in a helical pattern. As the second neuromodulation element 606 is deployed into the expanded treatment state, the second energy-delivery elements move into contact with an inner surface of a wall of the branch vessel 110a, 110b, 114 in which the second neuromodulation element 606 is deployed. Next, the method 400 includes using the second neuromodulation element 606 to modulate nerve tissue within a portion of the second and/or third anatomical regions 125b, 125c extending circumferentially around the branch vessel 110a, 110b, 114 in which the second neuromodulation element 606 is deployed (block 420).

After using the second neuromodulation element 606, the method 400 includes measuring a second degree of neuromodulation achieved via the second neuromodulation element 606 (block 422). If the second degree of neuromodulation is sufficient, the method 400 can end. If the second degree of neuromodulation is not sufficient, however, and if there are untreated branch vessels 110a, 110b, 114, the method 400 includes locating the second neuromodulation element 606 within one of the untreated branch vessels 110a, 110b, 114 while the second neuromodulation element 606 is in the low-profile delivery state (block 424) and redeploying the second neuromodulation element 606 (block 426). Next, the method 400 includes using the second neuromodulation element 606 to modulate nerve tissue within a portion of the second and/or third anatomical regions 125b, 125c extending circumferentially around the branch vessel 110a, 110b, 114 in which the second neuromodulation element 606 is redeployed (block 428). The method 400 further includes measuring a degree of neuromodulation achieved by using the second neuromodulation element 606 (block 430). This process can continue until the measured degree of neuromodulation is sufficient or there are no more untreated branch vessel 110a, 110b, 114. In FIG. 6, treatment of two additional branch vessels 110a, 110b, 114 is shown in dashed lines. In some cases, each treated branch vessel 110a, 110b, 114 is independently connected to the main vessel 102. In other cases, multiple branch vessels 110a, 110b, 114 can be treated along a single pathway extending from the main vessel 102 to the kidney 106.

In the embodiment illustrated in FIGS. 3-6, one catheter (i.e., the first catheter 502) is used to treat the first anatomical region 125a and another catheter (i.e., the second catheter 602) is used to treat the second and/or third anatomical regions 125b, 125c. Further, while the embodiment illustrated in FIGS. 3-6 describe treating the first anatomical region 125a followed by treating the second and/or third anatomical regions 125b, 125c, it should be understood that in other embodiments, the second and/or third anatomical regions 125b, 125c can be treated in a first instance (e.g., using the second catheter 602) or prior to treatment of the first anatomical region 125a. Optionally, a degree of neuromodulation can be assessed after treating the second and/or third anatomical regions 125b, 125c. In such embodiments, if the degree of neuromodulation is insufficient, the first anatomical region 125a can be treated (e.g., using the first catheter 502) following treatment of the second and/or third regions 125b, 125c. For example, in a specific example, the second catheter 602 can be used to treat the second and/or third anatomical region 125b, 125c (e.g., in one or more branch segments of the renal vasculature). If desirable, the first catheter 502 can be used subsequently to treat the first anatomical region 125a in a distalmost portion (e.g., a distal third of the main renal artery).

Figure 7:
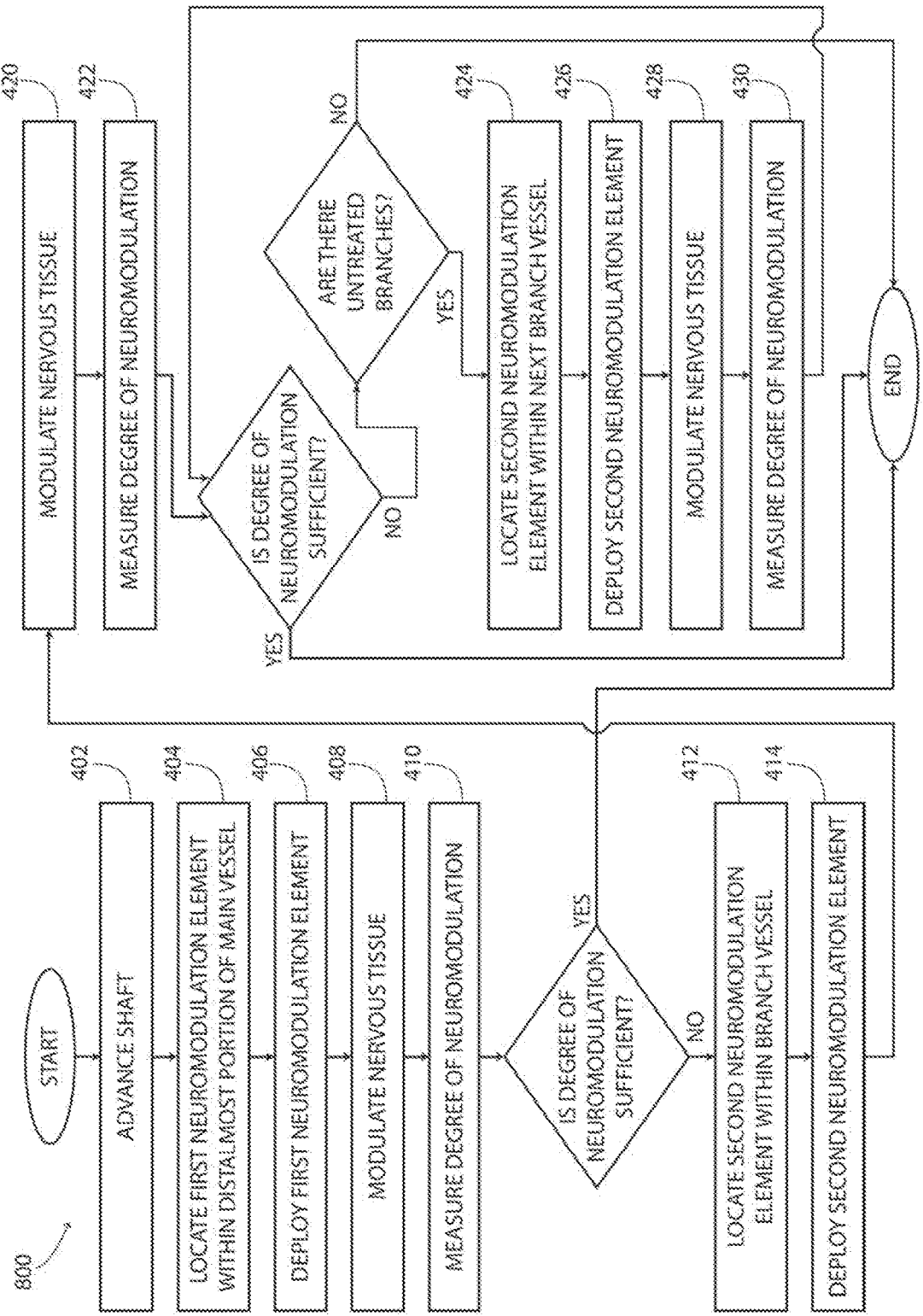
FIG. 7 is a flow chart illustrating a renal neuromodulation method in accordance with an embodiment of the present technology.

In other embodiments, a single catheter can be used to treat the first anatomical region 125a and the second and/or third anatomical regions 125b, 125c. FIGS. 7-12 illustrate such an embodiment. FIG. 7, for example, is a flow chart illustrating a renal neuromodulation method 800 in accordance with an embodiment of the present technology. The method 800 generally corresponds to the method 400 (FIG. 3) without the need to withdraw one shaft (e.g., the first shaft 504) and advance another shaft (e.g., the second shaft 604) if a first degree of neuromodulation is insufficient.

Figure 8:
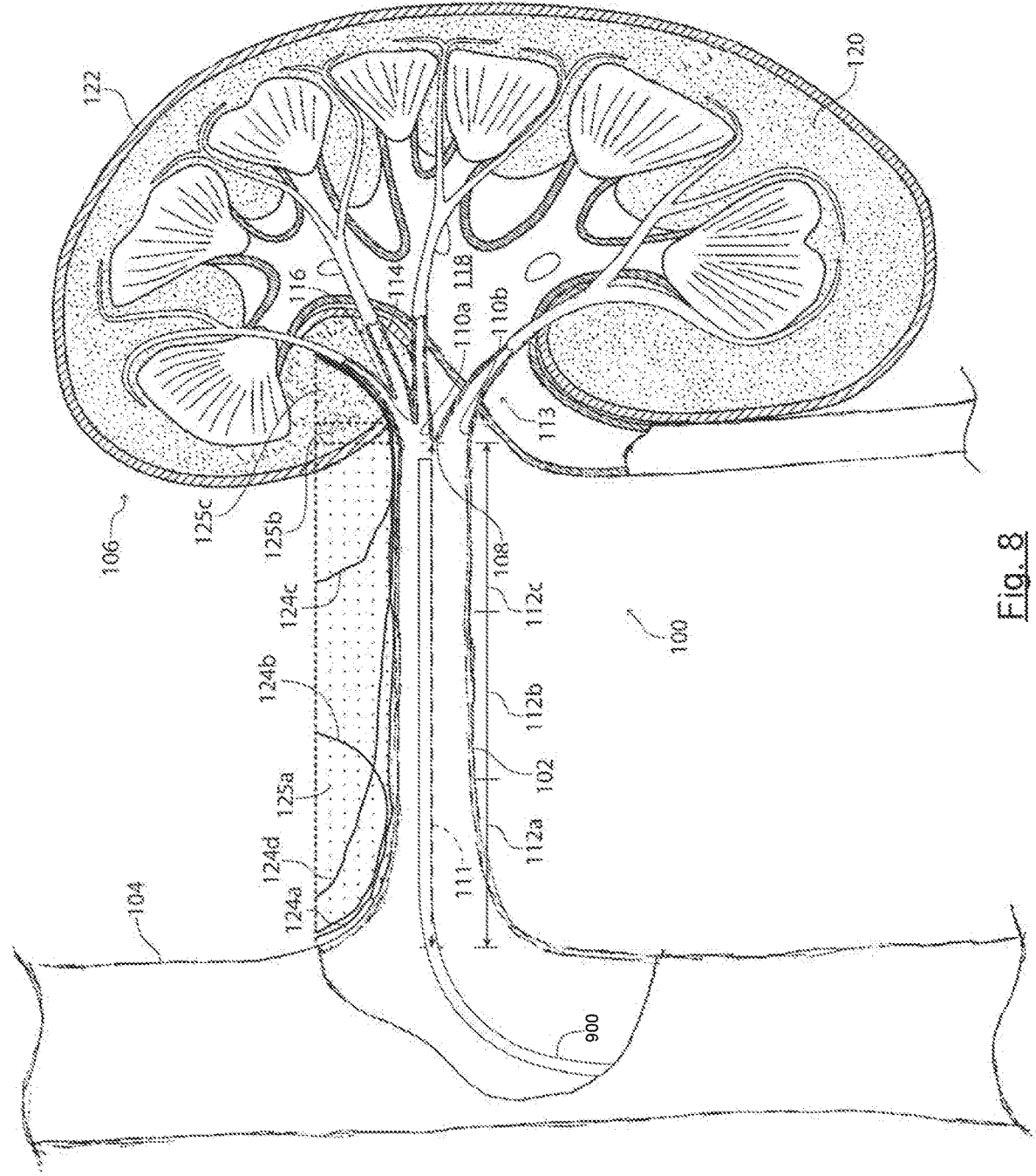
FIG. 8 is a partially cross-sectional profile view illustrating a sheath within the renal vasculature in accordance with an embodiment of the present technology. A catheter (not shown in FIG. 8) is disposed within the sheath. The catheter can include a first neuromodulation element and a second neuromodulation element in respective low-profile delivery states within the main vessel.
Figure 9:
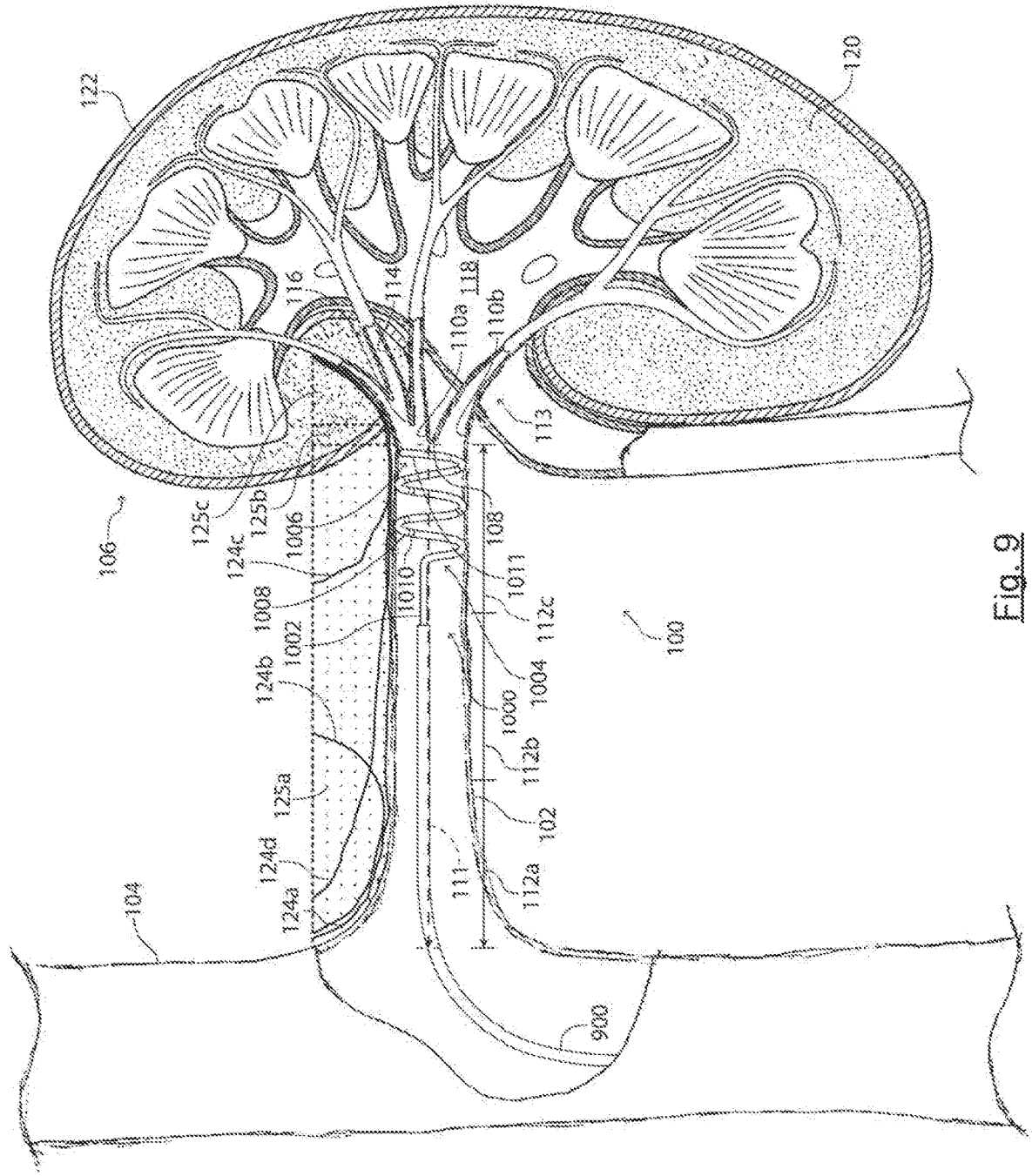
FIG. 9 is a partially cross-sectional profile view illustrating the sheath and the catheter of FIG. 8 within the renal vasculature in accordance with an embodiment of the present technology.
Figure 10:
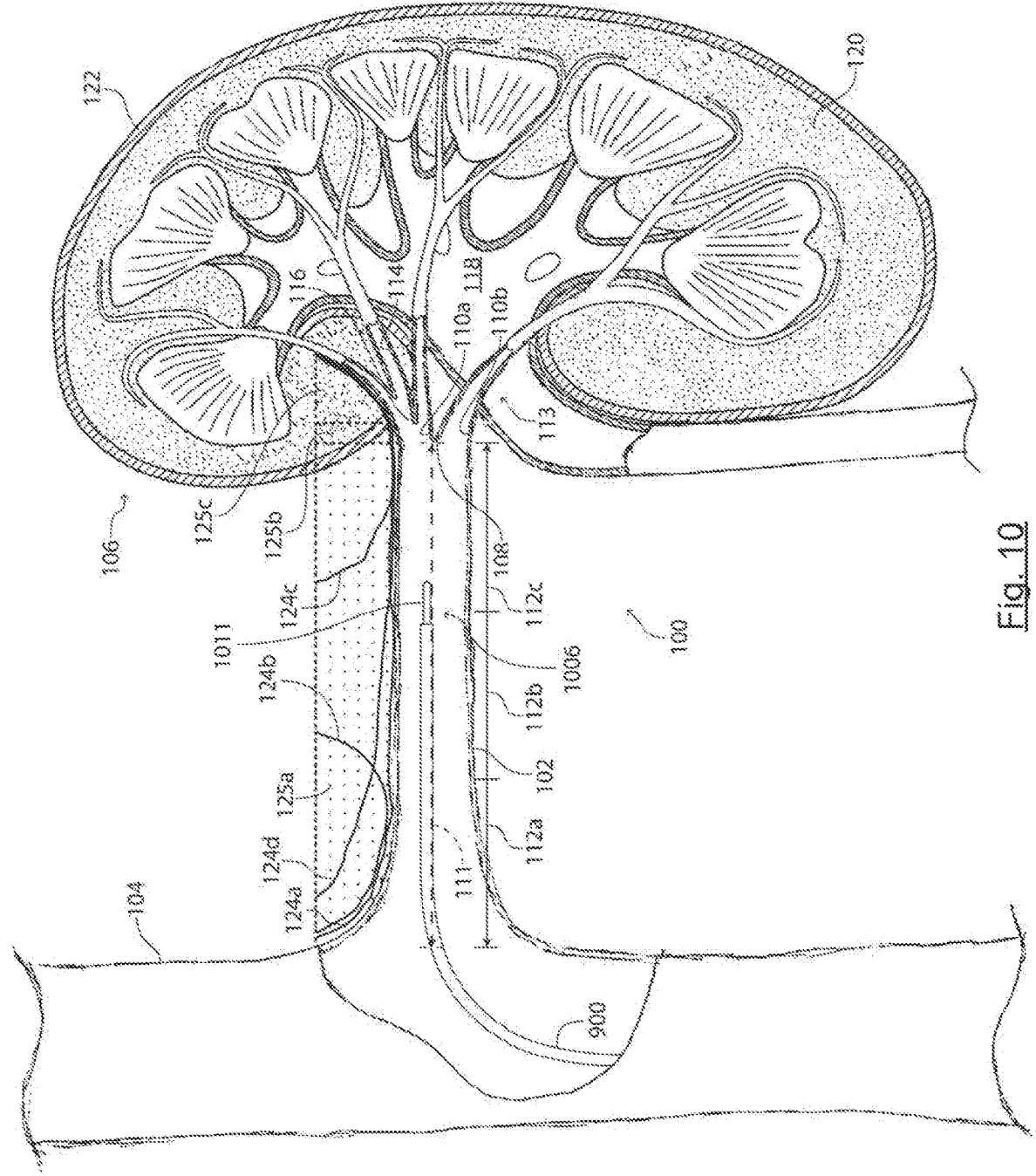
FIG. 10 is a partially cross-sectional profile view illustrating the sheath and the catheter of FIG. 8 within the renal vasculature in accordance with an embodiment of the present technology.
Figure 11:
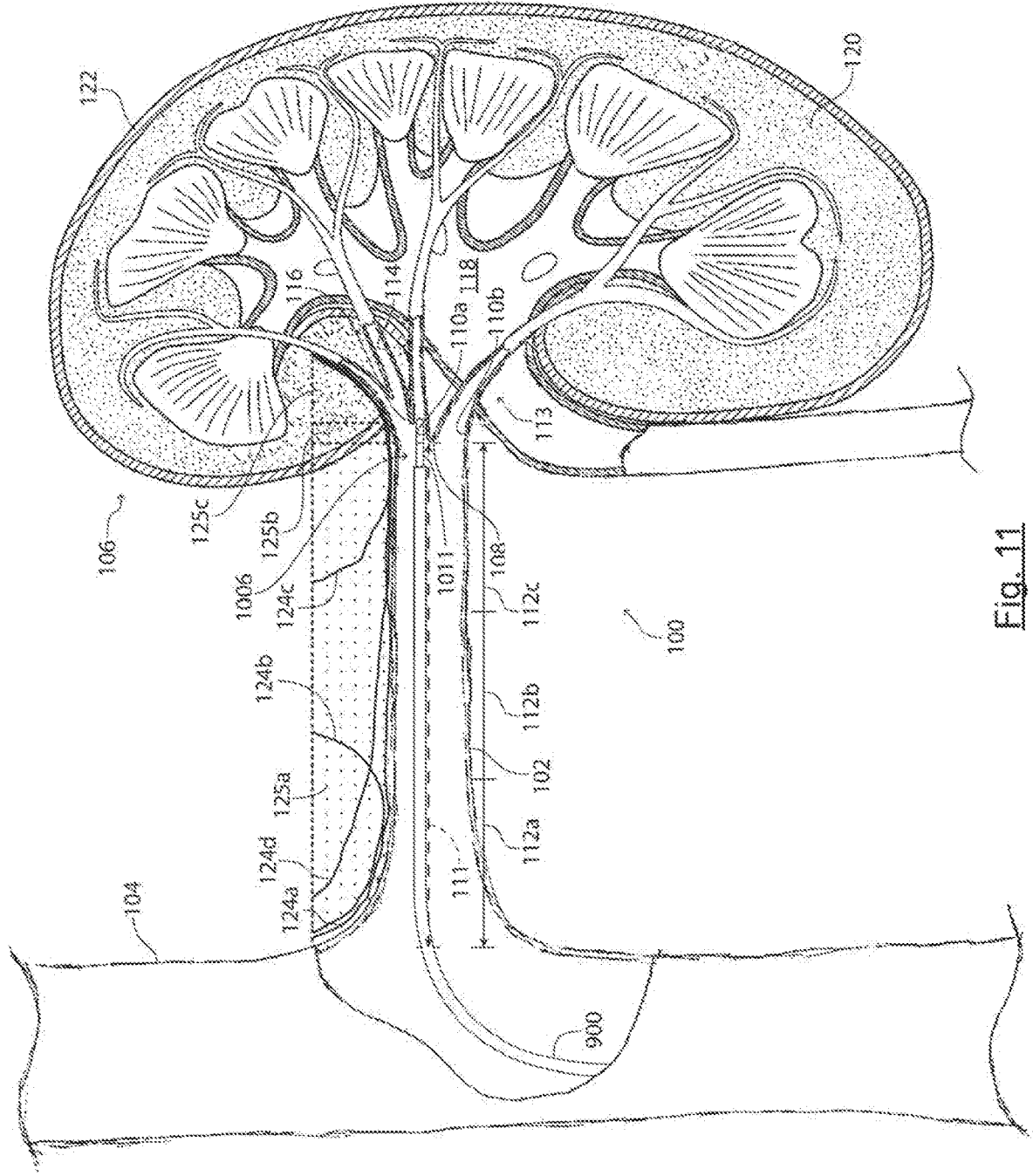
FIG. 11 is a partially cross-sectional profile view illustrating the sheath and the catheter of FIG. 8 within the renal vasculature in accordance with an embodiment of the present technology.
Figure 12:
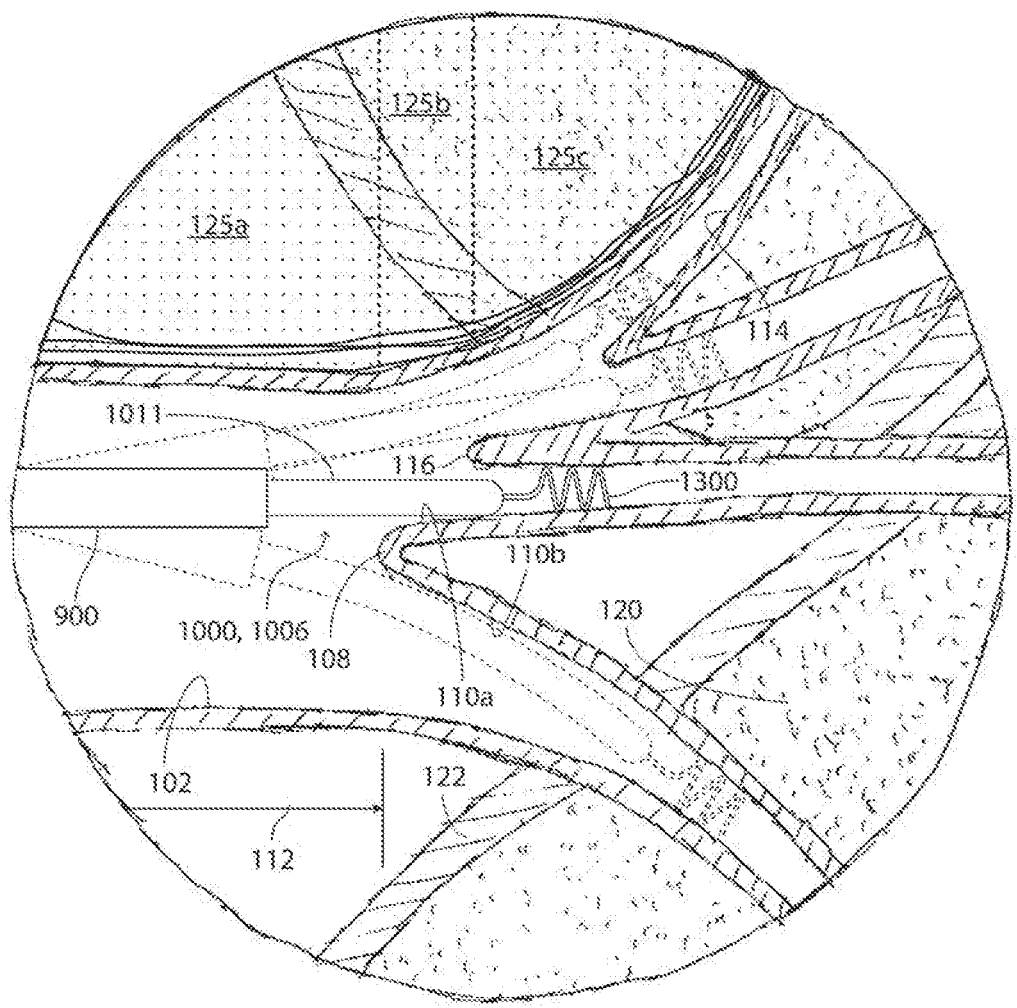
FIG. 12 is an enlarged, partially cross-sectional profile view illustrating the sheath and the catheter of FIG. 8 within the renal vasculature in accordance with an embodiment of the present technology.

FIG. 8 is a partially cross-sectional profile view illustrating a sheath 900 within the renal vasculature 100 at one point during the method 800. FIG. 9 is a partially cross-sectional profile view illustrating the sheath 900 and a catheter 1000 within the renal vasculature 100 at another point during the method 800. As shown in FIG. 9, the catheter 1000 includes an elongate shaft 1002 and a first neuromodulation element 1004 operably connected to the shaft 1002. FIGS. 10 and 11 are partially cross-sectional profile views illustrating the sheath 900 and a catheter 1000 within the renal vasculature 100 at still other respective points during the method 800. FIG. 12 is an enlarged, partially cross-sectional profile view illustrating the sheath 900 and one embodiment of the catheter 1000 within the renal vasculature 100 at yet another point during the method 800.

As shown in FIG. 9, the catheter 1000 includes a first neuromodulation element 1004 operably connected to the shaft 1002. In one embodiment, the first neuromodulation element 1004 can include an elongate support structure 1008 carrying a plurality of longitudinally spaced-apart electrodes 1010 (e.g., between about 2 electrodes and about 8 electrodes, greater than 2 electrodes, etc.). As shown in FIG. 9, the elongate support structure 1008 can have a helical/spiral form when unconstrained. In some embodiments, for example, the catheter 1000 can be delivered over a guidewire (not shown) and the guidewire can be retracted to release a preformed helical/spiral configuration of the support structure 1008. In other embodiments, the sheath 900 can be a straining sheath or guide catheter and the treatment catheter 1000 can be deployed into the helical/spiral form when pushed or otherwise presented distally from the sheath 900. Once deployed, the plurality of longitudinally spaced-apart electrodes 1010 can be positioned in apposition with an inner wall of the vessel lumen for treatment (e.g., neuromodulation of nervous tissue proximal the inner wall). Examples of suitable multi-electrode devices are described in U.S. patent application Ser. No. 13/281,360, filed Oct. 25, 2011, and incorporated herein by reference in its entirety. Other suitable devices and technologies, are described in U.S. patent application Ser. No. 13/279,330, filed Oct. 23, 2011, and additional thermal devices are described in U.S. patent application Ser. No. 13/279,205, filed Oct. 21, 2011, each of which are incorporated herein by reference in their entireties.

As shown in FIG. 9, the helical/spiral form of the elongate support structure 1008 can be deployed in the distalmost portion of the main vessel 102 and/or in one or more of the branch vessels 110a, 110b, 114. The helical/spiral shape can be longitudinally compressed, longitudinally stretched/elongated and/or be capable of accommodating a variety of anatomically restricted or expanded vessel architectures. As such, neuromodulation using the catheter 100 can result in a compressed spiral lesion pattern (e.g., lesions radially spaced about 2 mm apart), an elongated spiral lesion pattern (e.g., lesions longitudinally spaced about 2 mm to about 5 mm apart) and/or some combination of both a compressed and elongated spiral lesion pattern at one or more anatomical locations along the inner wall of the renal vasculature.

In several embodiments, the first neuromodulation element 1004 can be deployed in a branch vessel 110a, 110b, 114 and neuromodulation using the first neuromodulation element 1004 can result in a spiral/helical lesion pattern within the branch vessel. In particular embodiments, the spiral/helical lesion pattern can include a plurality of lesions formed along the branch vessel such that the proximal-most lesion is at least about 1 mm distal to the primary bifurcation. Accordingly, in some arrangements, one or more electrode(s) of the elongate support structure 1008 (e.g., the plurality of longitudinally spaced-apart electrodes 1010; FIG. 9) may be deselected such that only the selected electrode(s) deliver energy (e.g., RF energy) to the branch vessel for forming the lesion pattern. In one example, the elongate support structure 1008 can be inserted into a branch vessel 110a, 110b, 114 such that the proximal-most electrode(s) 1010 are distal to the primary bifurcation (e.g., about 1 to about 5 mm distal to the primary bifurcation, about 2 mm to about 6 mm distal to the primary bifurcation, about 5 mm distal to the primary bifurcation, etc.). In the event that the branch vessel 110a, 110b, 114 is short, narrow or the distal-most portion of the branch vessel is not desirable for treatment, the distal-most electrode(s) 1010 can be selectively deselected from delivering energy (e.g., RF energy) to the branch vessel wall during treatment. In another example, the elongate support structure 1008 can be inserted into a branch vessel 110a, 110b, 114 such that a portion of the electrodes 1010 are positioned within the branch vessel and a proximal portion of the elongate support structure 1008 can be positioned across the primary bifurcation, In this example, electrode(s) 1010 at or near the primary bifurcation (e.g., proximal-most electrode(s)) can be deselected prior to treatment such that energy will not be delivered via the deselected electrode(s).

In some embodiments, more than one branch vessel 110a, 110b, 114 can be treated. In a particular example, all accessible branch vessels can be treated. Following neuromodulation of the one or more branch vessels 110a, 110b, 114, the first neuromodulation element can be retracted proximally to a segment (e.g., the distalmost portion, the central portion, the proximal portion) of the main vessel 102 for administering additional treatment(s). In various arrangements, the first neuromodulation element can be repositioned proximally from the branch vessel 110a, 110b, 114 to the main vessel 102 while fully deployed, partially compressed, or fully compressed into a low-profile delivery state before administering treatment to the main vessel 102.

Referring to FIG. 9, and in another embodiment, the catheter 1000 can optionally include a second neuromodulation element 1006 operably connected to the shaft 1002 and/or the first neuromodulation element 1004. The second neuromodulation element 1006 can include an elongate conduit 1011 directly connected to a distal end of the support structure 1008. For example, in the embodiment shown in FIG. 12, the second neuromodulation element 1006 further includes a wire electrode 1300. The support structure 1008 and the wire electrode 1300 can have respective helical/spiral forms when unconstrained. In another embodiment, the second neuromodulation element 1006 includes an elongate support structure similar to the support structure 1008 and includes electrodes similar to the electrodes 1010. Other variations of the first and second neuromodulation elements 1004, 1006 are also possible.

In FIG. 8, the first and second neuromodulation elements 1004, 1006 are in their respective low-profile delivery states within the sheath 900. The shaft 1002 can be advanced to the renal vasculature 100 with the first and second neuromodulation elements 1004, 1006 in these respective low-profile delivery states. For example, the sheath 900 and the conduit 1011 can constrain the support structure 1008 and the wire electrode 1300, respectively, into generally linear forms. As shown in FIG. 9, when the first neuromodulation element 1004 is at a desired position within the renal vasculature 100, constraint on the support structure 1008 can be reduced, such as by uncovering the support structure 1008 from within the sheath 900. This causes the support structure 1008 to assume its helical/spiral form, thereby moving the electrodes 1010 toward an inner surface of a wall of the main vessel 102.

As shown in FIG. 10, after delivering energy to the nerve fibers 124 within a distal portion of the first anatomical region 125a, the support structure 1008 is retracted relative to the sheath 900 and/or the sheath 900 advanced relative to the support structure 1008 to force the support structure 1008 back into its low-profile delivery state. The second neuromodulation element 1006 may remain protruding from a distal end of the sheath 900. As shown in FIG. 11, the second neuromodulation element 1006 can then be positioned within one of the branch vessels 110a, 110b, 114 while the wire electrode 1300 is in its low-profile delivery state. When the second neuromodulation element 1006 is properly positioned (as shown in FIG. 12), the second neuromodulation element 1006 is deployed into an expanded treatment state. For example, the wire electrode 1300 can be pushed distally out of the conduit 1011 (e.g., by pushing a control wire (not shown)) distally. This is expected to reduce constraint on the wire electrode 1300 such that the wire electrode 1300 assumes its helical/spiral form and contacts an inner surface of a wall of the branch vessel 110a, 110b, 114. In another example, the second neuromodulation element 1006 can have a single element tapering distally (e.g., a cross-sectional dimension of the second neuromodulation element 1006 may decrease from proximal to distal) to accommodate the inferior dimensions of the branch vessels 110a, 110b, 114. In these and other cases, the first and second neuromodulation elements 1004, 1006 can be continuous. For example, a distal portion of a single elongate support element can be deployed within one of the branch vessels 110a, 110b, 114 while a proximal portion of the same element is deployed within the distal portion of the main vessel 102. This can allow nerve fibers 124 on both sides of the primary bifurcation 108 to be treated simultaneously or consecutively, if desired.

Although FIGS. 7-12 illustrate neuromodulation of nerve tissue in the anatomical region 125a surrounding the main vessel 102 prior to neuromodulation of the nerve tissue in the anatomical regions 125b, 125c surrounding the branches 110a, 110b, 114, it should be understood that, in some embodiments, the anatomical regions 125b, 125c may be treated prior to the anatomical region 125a surrounding the main vessel 102.

With reference again to FIGS. 7-12 together, after reducing constraint on the wire electrode 1300, the method 800 includes using the second neuromodulation element 1006 to modulate nerve tissue within a portion of the second and/or third anatomical regions 125b, 125c extending circumferentially around the branch vessel 110a, 110b, 114 in which the second neuromodulation element 1006 is deployed. In FIG. 12, treatment of the second primary branch vessel 110b and two additional subordinate branch vessels 114 is shown in dashed lines. With respect to some embodiments, the dashed lines represent sequential treatment of these additional vessels. In another embodiment, the second neuromodulation element includes multiple wire electrodes 1300 that are individually guided into respective additional vessels. With respect to these embodiments, the dashed lines represent simultaneous treatment of the additional vessels.

Figure 13:
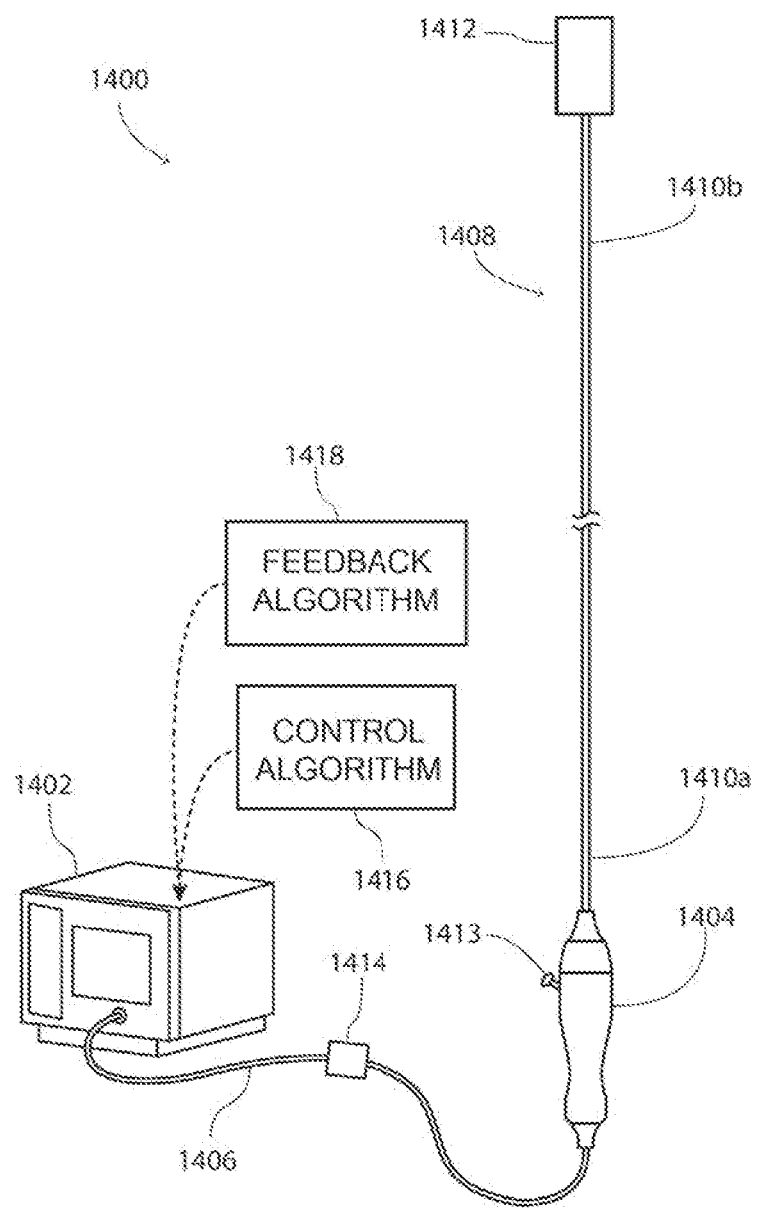
FIG. 13 is a perspective view illustrating a neuromodulation system configured in accordance with an embodiment of the present technology.

Any one of the catheters described above with references to FIGS. 1-12 can be incorporated into a suitable neuromodulation system. FIG. 13, for example, is a partially schematic perspective view illustrating a neuromodulation system 1400 configured in accordance with one embodiment of the present technology. The system 1400 includes a console 1402, a catheter 1408, and a cable 1406 extending therebetween. The catheter 1408 can be identical or similar to any of the catheters described herein. The catheter 1408, for example, includes a handle 1404 and an elongate shaft 1410 having a proximal end portion 1410a and a distal end portion 1410b. The catheter 1408 further includes a neuromodulation element 1412 at the distal end portion 1410b of the shaft 1410. The shaft 1410 is configured to locate the neuromodulation element 1412 at a treatment location within a body lumen, such as a suitable blood vessel, duct, airway, or other naturally occurring lumen within the human body at any suitable branching level. Once located, the neuromodulation element 1412 is configured to provide or support a neuromodulation treatment.

The console 1402 is configured to control, monitor, supply energy to, and/or otherwise support operation of the catheter 1408. Alternatively, the catheter 1408 can be self-contained or otherwise configured for operation without connection to the console 1402. When present, the console 1402 can be configured to generate a selected form and/or magnitude of energy for delivery to tissue at a treatment location via the neuromodulation element 1412. The console 1402 can have different configurations depending on the treatment modality of the catheter 1408. For example, when the catheter 1408 is configured for electrode-based, heat-element-based, or transducer-based treatment, the console 1402 can include an energy generator (not shown) configured to generate radio frequency (RF) energy (e.g., monopolar and/or bipolar RF energy), pulsed electrical energy, microwave energy, optical energy, ultrasound energy (e.g., high-intensity focused ultrasound energy), direct heat, radiation (e.g., infrared, visible, and/or gamma radiation), and/or one or more other suitable types of energy.

The system 1400 can include a mechanical control device 1413 (e.g., a lever) configured to mechanically control operation of one or more components of the catheter 1408. The system 1400 can further include an electrical control device 1414 configured to electrically control operation of one or more components of the catheter 1408 directly and/or via the console 1402. The electrical control device 1414 can be disposed along the cable 1406 as shown in FIG. 13, incorporated into the handle 1404, or have another suitable position within the system 1400. During use of the system 1400, an operator can use the electrical control device 1414 to provide instructions to the console 1402, such as to initiate or terminate a neuromodulation treatment, operatively deselect electrode(s) in multi-electrode neuromodulation elements, etc. In addition to being configured to execute such instructions, the console 1402 can be configured to execute an automated control algorithm 1416. Furthermore, the console 1402 can be configured to provide information to an operator before, during, and/or after a neuromodulation procedure via a feedback algorithm 1418. Feedback from the feedback algorithm 1418 can be audible, visual, haptic, or have another suitable form. The feedback can be based on output from a monitoring system (not shown). For example, such a monitoring system can include a monitoring device (e.g., a sensor) configured to measure a condition at a treatment location (e.g., a temperature of tissue being treated), a systemic condition (e.g., a patient vital sign), or another condition germane to the treatment, health, and/or safety of a patient. The monitoring device can be integrated into the catheter 1408 or separate from the catheter 1408.

In some embodiments of a renal neuromodulation procedure (as an example, a procedure using a spiral/helical neuromodulation element), one or more ablations may be performed in any (e.g., all) renal vessels (e.g., renal arterial vessels) greater than 3 mm and less than 8 mm in diameter (e.g., accessory, branch and/or main renal arteries). In certain embodiments, initial placement of a renal neuromodulation element may be just proximal to the renal parenchyma (e.g., as identified on fluoroscopic imaging). In some embodiments, an operator may perform as many ablations within a segment as anatomy permits, starting distally and working proximally, without forming overlapping treatment zones. In certain embodiments, an operator may avoid forming ablations in a carina. In methods in which a multielectrode neuromodulation element (e.g., a multielectrode spiral/helical neuromodulation element, such as one including four or five electrodes) is used, if the vessel segment cannot accommodate all electrodes, then the operator may, for example, either 1) position a smaller number of electrodes and deselect proximal electrodes, or 2) advance all electrodes within the renal artery vessel segment and deselect the distal electrodes.

Renal Neuromodulation

Renal neuromodulation is the partial or complete incapacitation or other effective disruption of nerves of the kidneys (e.g., nerves terminating in the kidneys or in structures closely associated with the kidneys). In particular, renal neuromodulation can include inhibiting, reducing, and/or blocking neural communication along nerve fibers (e.g., efferent and/or afferent nerve fibers) of the kidneys. Such incapacitation can be long-term (e.g., permanent or for periods of months, years, or decades) or short-term (e.g., for periods of minutes, hours, days, or weeks). Renal neuromodulation is expected to contribute to the systemic reduction of sympathetic tone or drive and/or to benefit at least some specific organs and/or other bodily structures innervated by sympathetic nerves. Accordingly, renal neuromodulation is expected to be useful in treating clinical conditions associated with systemic sympathetic overactivity or hyperactivity, particularly conditions associated with central sympathetic overstimulation. For example, renal neuromodulation is expected to efficaciously treat hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions. Such clinical conditions may be the result of physiological parameters associated with systemic sympathetic overactivity or hyperactivity such as elevated blood pressure, elevated blood sugar levels, ovarian cysts, etc.

Renal neuromodulation can be electrically-induced, thermally-induced, or induced in another suitable manner or combination of manners at one or more suitable treatment locations during a neuromodulation procedure. The treatment location can be within or otherwise proximate to renal vasculature (e.g., a renal artery, a ureter, a renal pelvis, a major renal calyx, a minor renal calyx, or another suitable structure), and the treated tissue can include tissue at least proximate to a wall of the renal lumen. For example, with regard to a renal artery, a neuromodulation procedure can include modulating nerves in the renal plexus, which lay intimately within or adjacent to the adventitia of the renal artery. Various suitable modifications can be made to the catheters described above to accommodate different treatment modalities. For example, the electrodes 1010 (FIG. 9) can be replaced with transducers to facilitate transducer-based treatment modalities.

Renal neuromodulation can include an electrode-based or treatment modality alone or in combination with another treatment modality. Electrode-based or transducer-based treatment can include delivering electricity and/or another form of energy to tissue at or near a treatment location to stimulate and/or heat the tissue in a manner that modulates nerve function. For example, sufficiently stimulating and/or heating at least a portion of a sympathetic renal nerve can slow or potentially block conduction of neural signals to produce a prolonged or permanent reduction in renal sympathetic activity (e.g., reducing sympathetic neural activity). A variety of suitable types of energy can be used to stimulate and/or heat tissue at or near a treatment location. For example, neuromodulation in accordance with embodiments of the present technology can include delivering RF energy, pulsed electrical energy, microwave energy, optical energy, focused ultrasound energy (e.g., high-intensity focused ultrasound energy), and/or another suitable type of energy. An electrode or transducer used to deliver this energy can be used alone or with other electrodes or transducers in a multi-electrode or multi-transducer array.

Neuromodulation using focused ultrasound energy (e.g., high-intensity focused ultrasound energy) can be beneficial relative to neuromodulation using other treatment modalities. Focused ultrasound is an example of a transducer-based treatment modality that can be delivered from outside the body. Focused ultrasound treatment can be performed in close association with imaging (e.g., magnetic resonance, computed tomography, fluoroscopy, ultrasound (e.g., intravascular or intraluminal), optical coherence tomography, or another suitable imaging modality). For example, imaging can be used to identify an anatomical position of a treatment location (e.g., as a set of coordinates relative to a reference point). The coordinates can then entered into a focused ultrasound device configured to change the power, angle, phase, or other suitable parameters to generate an ultrasound focal zone at the location corresponding to the coordinates. The focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array, which can be curved or straight.

Heating effects of electrode-based or transducer-based treatment can include ablation and/or non-ablative alteration or damage (e.g., via sustained heating and/or resistive heating). For example, a neuromodulation procedure can include raising the temperature of target nerve fibers to a target temperature above a first threshold to achieve non-ablative alteration, or above a second, higher threshold to achieve ablation. The target temperature can be higher than about body temperature (e.g., about 37° C.) but less than about 45° C. for non-ablative alteration, and the target temperature can be higher than about 43° C. for ablation. Heating tissue to a temperature between about body temperature and about 43° C. can induce non-ablative alteration with reversible consequences, for example, via moderate heating of target nerve fibers or of luminal structures that perfuse the target nerve fibers. In cases where luminal structures are affected, the target nerve fibers can be denied perfusion resulting in necrosis of the nerve tissue. Heating tissue to a target temperature higher than about 43° C. (e.g., higher than about 60° C.) can induce ablation, for example, via substantial heating of target nerve fibers or of luminal structures that perfuse the target fibers. In some patients, it can be desirable to heat tissue to temperatures that are sufficient to ablate the target nerve fibers or the luminal structures, but that are less than about 90° C. (e.g., less than about 85° C., less than about 80° C., or less than about 75° C.).

EXPERIMENTAL EXAMPLES

Example 1

This section describes an example of the outcome of renal neuromodulation on animal subjects. In this example, and referring to FIG. 14, studies using the pig model have been performed directed to modulation of nerve tissue at different treatment sites within the renal vasculatures using a multi-electrode Symplicity Spyral™ catheter or a single-electrode Symplicity Flex™ catheter, from Medtronic, Inc., of 710 Medtronic Parkway, Minneapolis, MN 55432-5604. Renal cortical norepinephrine (NE) concentration was used as a surrogate marker to measure procedural efficacy.

Figure 14:
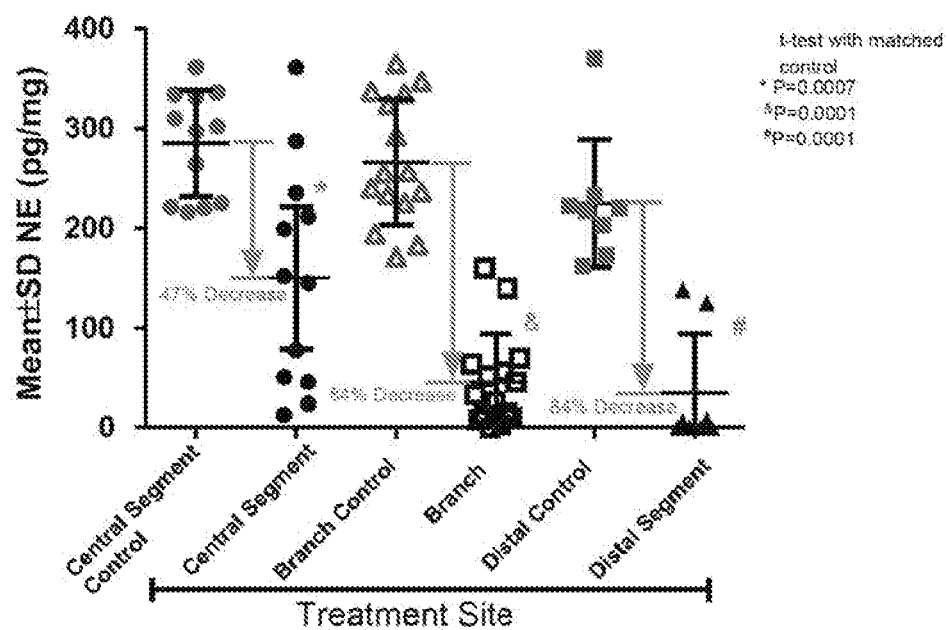
FIG. 14 is a plot of mean norepinephrine concentration before and after renal neuromodulation procedures performed at different treatment sites within the renal vasculatures of animal subjects.

FIG. 14 is a plot of mean NE concentration before and after renal neuromodulation procedures performed at the central segment (e.g., "Central") of the main renal artery, the distal segment (e.g., "Distal") of the main renal artery, and in two renal artery branches (e.g., "Branch") of pig subjects. For pigs undergoing treatment of a branch vessel site, a Symplicity Spyral™ catheter was inserted entirely into the cranial renal artery branch and used to treat the branch with four lesions at the furthest distance into the branch vessel that could accommodate the device given dimensional constraints. The catheter was then withdrawn into the main renal vessel and then advanced under fluoroscopy into the caudal renal artery branch and treatment procedure was repeated. In all cases with three or more renal artery branches only the cranial and caudal branch were treated. Accordingly, the multi-electrode device was advanced so that the electrodes were inserted as far as possible into the branches. For pigs undergoing distal main renal artery treatment, six lesions were formed at the distal segment of the renal artery and within a distance of 6 mm proximal to the branch point within the renal artery using the Symplicity Flex™ catheter (FIG. 14, "Distal Portion"). The longitudinal spacing between the lesions was approximately 2 mm, with a lesion footprint of approximately 2 mm each. In this experimental example, a first lesion was formed about 5-6 mm from the bifurcation. The catheter was then proximally retracted 1-2 mm (e.g., maximum of 2 mm) and rotated 90 degrees followed by formation of a second lesion. Further lesions were formed by sequential movement of the catheter proximally 1-2 mm, rotation of 90 degrees followed by lesion formation. As such, a longitudinal separation of lesions occurred approximately 1-2 mm apart along the longitudinal length of the distal segment of the main renal artery. For pigs undergoing main artery treatment at a central segment of the main renal artery, a Symplicity Flex™ catheter was used to form between 4 and 6 ablations in a spiral/helical pattern along the central segment of the main renal artery. In these animals, the first lesion was placed approximately 5 mm proximal to the bifurcation. Each subsequent lesion was placed 5 mm proximally and rotated at 90 degrees forming a spiral/helical pattern.

As shown in FIG. 14, mean renal cortical NE levels dropped approximately 84% between control and experimental groups for pigs undergoing treatment at the distal segment of the main renal artery or at a branch artery. Pigs undergoing treatment at the central segment of the main renal artery exhibited an approximate 47% decrease in mean NE levels following treatment. Accordingly, the distal segment and branch treatment sites exhibited an increased effectiveness of neuromodulation as compared to treatment at the central segment as indicated by NE concentration in renal tissue (FIG. 14).

These findings suggest that the positioning of the treatment device within the renal vasculature at a branch vessel or a distal portion of the main renal artery, as measured by NE concentration in renal tissue, results in increased efficacy of modulation of targeted renal nerves. These findings also suggest that the position in the distal segment of the main renal artery (e.g., distalmost third of the main renal vessel, distalmost quarter of the main renal vessel, approximately 1 cm proximal of the branch point to approximately 6 cm proximal of the branch point, between approximately 1 cm and approximately 10 cm proximal of the main renal vessel bifurcation, etc.) can provide a target for RF nerve ablation due to the proximity of the renal nerves. For example, in some embodiments, a compressed spiral/helical lesion pattern in a segment of the renal artery wherein the renal nerves are consistently in closer proximity to the inner wall of the renal vessel can effectively treat more nerves than a set of helical lesions spaced further apart along the full length of the main renal artery where distribution of the renal nerves vary in number, orientation and proximity to the to the inner wall of the renal vessel.

Example 2

Example 2 also describes the outcome of renal neuromodulation on animal subjects in an additional experiment.

Figures 15A, 15B:
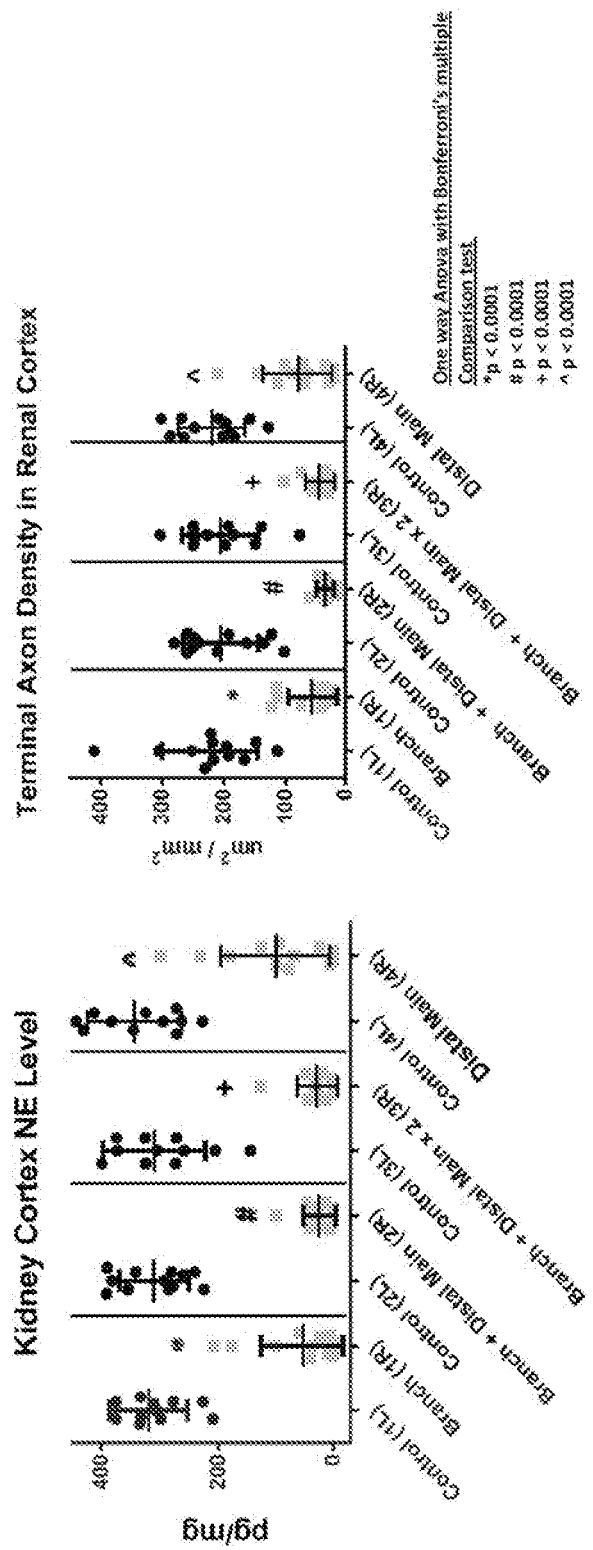
FIG. 15A is another plot of mean norepinephrine concentration before and after renal neuromodulation procedures performed in the distal portions of the main renal artery, the renal arterial branches, and the combination of the distal portions of the main renal artery and the renal arterial branches of animal subjects.
FIG. 15B is a plot of terminal axon density in the renal cortex corresponding to the treatment sites within the renal vasculature of the animal subjects shown in FIG. 15A.

In this example, and referring to FIGS. 15A and 15B, studies using the pig model have been performed directed to modulation of nerve tissue at different treatment sites and/or different combinations of treatment sites within the renal vasculature using a multi-electrode Symplicity Spyral™ catheter or a single-electrode Symplicity Flex™ catheter along with a Symplicity G3™ generator. The catheters and generator are from Medtronic, Inc. Renal cortical NE concentration (FIG. 15A) and terminal axon density in the renal cortex (FIG. 15B) were used as markers to measure procedural efficacy.

FIG. 15A is a plot of mean NE concentration before and after renal neuromodulation procedures performed at the distal segment (e.g., distal third) of the main renal artery (e.g., "Distal Main"), in two renal artery branches (e.g., "Branch"), at the renal artery branches and the main renal artery (e.g., "Branch+Main"), and at the renal artery branches and two cycles of treatment in the main renal artery (e.g., "Branch+Main x2") of pig subjects (N=12 pigs). For pigs undergoing treatment of a branch vessel site, a Symplicity Spyral™ catheter was inserted into the first renal artery branch (e.g., the cranial branch) and used to treat the branch with up to four lesions (e.g., 2 lesions, 3 lesions, 4 lesions) with distalmost electrodes being optionally and selectively deactivated in some instances in which the branch vessel was short, narrow, or otherwise undesirable for treatment. The catheter was placed in the first branch location such that the proximal-most electrode was distal to the bifurcation and, when deployed, the lesions were approximately 2 mm apart. The catheter was then withdrawn into the main renal vessel and then advanced under fluoroscopy into the second renal artery branch (e.g., the caudal branch) and the treatment procedure was repeated. In all cases with three or more renal artery branches only the cranial and caudal branch were treated. Accordingly, the multi-electrode device was advanced such that the first electrode (e.g., proximal electrode) was placed approximately 1-3 mm distal to the bifurcation.

For pigs undergoing distal main renal artery treatment, six lesions were formed at the distal segment of the renal artery and within a distance of 6 mm proximal to the branch point within the renal artery using the Symplicity Flex™ catheter (FIGS. 15A-15B, "Distal Main"). The longitudinal spacing between the lesions was approximately 2 mm, with a lesion footprint of approximately 2 mm each. In this experimental example, a first lesion was formed about 5-6 mm proximal to the bifurcation. The catheter was then proximally retracted 1-2 mm (e.g., maximum of 2 mm) and rotated 90 degrees followed by formation of a second lesion. Further lesions were formed by sequential movement of the catheter proximally 1-2 mm, rotation of 90 degrees followed by lesion formation. As such, a longitudinal separation of lesions occurred approximately 1-2 mm apart along the longitudinal length of the distal segment of the main renal artery.

In pigs undergoing a combination treatment approach that includes both treatment of the branches and the distal portion of the main renal artery, a Symplicity Spyral™ catheter was inserted into the first renal artery branch for treatment, followed by the second renal artery branch for treatment, and finally retracted and deployed for treatment in the distal portion of the main renal artery.

As shown in FIG. 15A, mean renal cortical NE levels dropped approximately greater than 80% between control and experimental groups for pigs undergoing treatment at the distal segment of the main renal artery (e.g., "Distal Main") or at the branch arteries (e.g., "Branch"). Neuromodulation in these pigs also resulted in approximately 70% reduction ("Distal Main") and greater than 80% reduction ("Branch") in cortical axonal density (FIG. 15B). In this example, untreated or undertreated segments (e.g., branches treated with only 2 or 3 lesions) can give rise to outliers in the data set (e.g., note two outliers approaching 200 pg/mg NE in the treated branch column "Branch (1R)" of FIG. 15A). Pigs undergoing a combination treatment approach that combined treatment of the branches and the distal portion of the main renal artery using a Symplicity Spyral™ catheter demonstrated a greater than 90% reduction in mean renal NE concentration. The 90% reduction in NE was corroborated with a 92% reduction terminal axon density as shown in FIG. 15B. Pigs undergoing another combination treatment approach that combined treatment of the branches and two treatment cycles of the distal portion of the main renal artery using a Symplicity Spyral™ catheter also exhibited a greater than 90% reduction in mean renal NE concentration levels and a 90% reduction in terminal axon density following treatment (FIGS. 15A and 15B, respectively), but did not statistically improve the response more than the combination treatment approach that included a single cycle of treatment in the main renal artery. Accordingly, the branch treatment sites combined with treatment of the distal portion of the main renal artery exhibited an increased effectiveness of neuromodulation as compared to treatment at the distal segment or the branches alone as indicated by NE concentration levels and terminal axon density in renal tissue (FIGS. 15A and 15B).

These findings suggest that the positioning of the treatment device within the renal vasculature at a branch vessel for treatment followed by treatment of the main renal artery, as measured by NE concentration in renal tissue and histologically by measuring terminal axon density in the renal cortex, is expected to result in increased efficacy of modulation of targeted renal nerves. These findings also suggest that a combination approach of treating the branches (e.g., at least two branches) in addition to one or more segments of the main renal artery (e.g., the proximal portion, the central portion, the distalmost third of the main renal vessel, distalmost quarter of the main renal vessel, approximately 1 cm proximal of the branch point to approximately 6 cm proximal of the branch point, between approximately 1 cm and approximately 10 cm proximal of the main renal vessel bifurcation, etc.), can provide a targeted therapeutic approach for RF nerve ablation. Without being bound by theory, the targeted therapeutic approach for RF nerve ablation is expected to have higher efficacy in the combined treatment approach in certain instances due to the proximity of the renal nerves to the renal vessel wall in the distal segment of the main renal artery (e.g., distalmost third of the main renal vessel, distalmost quarter of the main renal vessel, approximately 1 cm proximal of the branch point to approximately 6 cm proximal of the branch point, between approximately 1 cm and approximately 10 cm proximal of the main renal vessel bifurcation, etc.) and in the branches. Additionally, by combining the treatment locations (e.g., branches and main renal artery) into a treatment session, more renal nerves may be ablated.

Example 3

Example 3 describes the outcome of catheter-based renal neuromodulation on animal subjects in an additional experiment. In this example (and referring to FIGS. 16A and 16B), studies using the pig model were performed using a multi-electrode Symplicity Spyral™ catheter or a single-electrode Symplicity Flex™ catheter along with a Symplicity G3™ generator. The catheters and generator are from Medtronic, Inc. The catheters were used in a number of animals (n=66) to create multiple RF ablations in the renal vasculature. Cortical axon density in the renal cortex (FIG. 16A) and renal cortical NE concentration (FIG. 16B) were used as markers to measure procedural efficacy.

As shown in FIG. 16A, cortical axon area (per $mm^2$) dropped approximately greater than 54% between a control group (n=64) and treated groups of pigs (n=66) undergoing treatment. For pigs undergoing treatment with the Symplicity Flex™ catheter (n=54), an average of 4.1 lesions were formed in each animal. These pigs demonstrated a 56.9% increase in non-functional axonal area along the renal artery, and a 68% decrease in cortical axon area as compared with the control group. For pigs undergoing treatment with the Symplicity Spyral™ catheter (n=12), an average of 4.0 lesions were formed in each animal. The pigs undergoing treatment with the Symplicity Spyral™ catheter demonstrated a 47.3% increase in non-functional area along the renal artery, and a 54% decrease in cortical axon area relative to the control group. Without being bound by theory, it is believed that the loss of cortical axons is a likely consequence of nerve atrophy distal to the ablation sites.

Figure 16B:
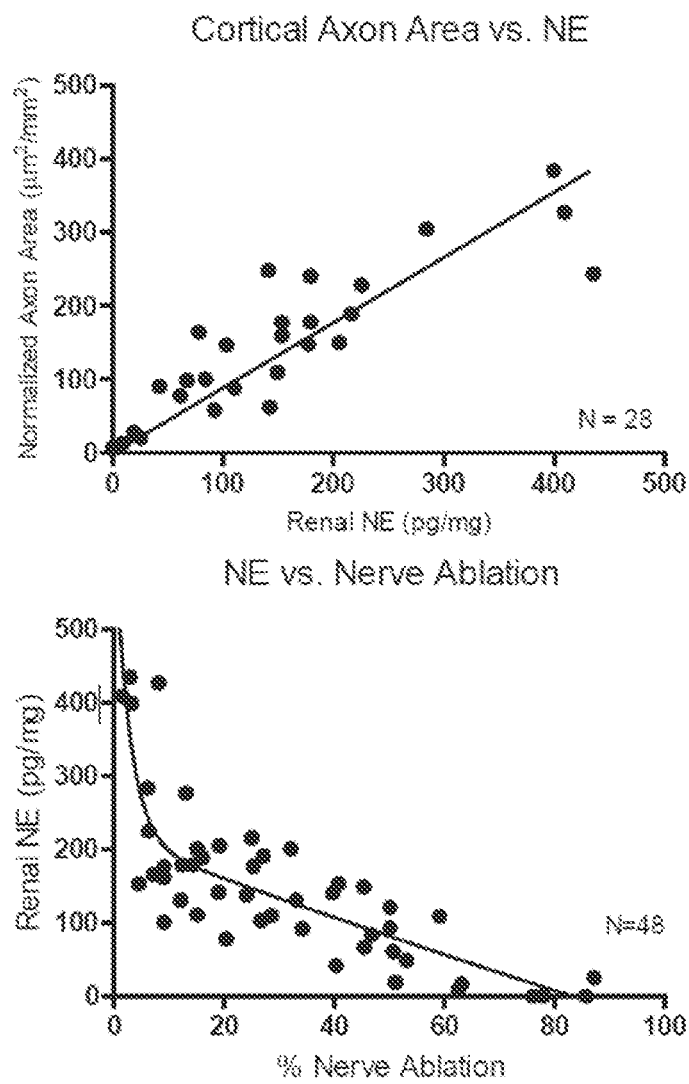
FIG. 16B is a series of graphs illustrating the response correlation between normalized cortical axon area vs. norepinephrine concentration and norepinephrine concentration vs. extent of nerve ablation along the artery of the animal subjects of FIG. 16A.

FIG. 16B includes (a) a graph of normalized cortical axon area vs. renal NE concentration, and (b) a graph of renal NE concentration vs. extent (%) of nerve ablation. Referring to the table of FIG. 16A and the two graphs of FIG. 16B together, cortical axon area correlates directly with renal NE. In particular, pigs undergoing treatment with the Symplicity Flex™ catheter exhibited a 65% decrease in mean NE level compared with the pigs in the control group. The pigs treated with the Symplicity Spyral™ catheter exhibited a 68% decrease in mean NE level. This is further shown by the first graph of FIG. 16B, which demonstrates that a decrease in cortical axon area correlates with a decrease in NE levels. Referring to the second graph of FIG. 16B, renal NE decrease is non-linear with increased loss of nerve viability along the artery (further extent (%) of nerve ablation). These findings suggest that catheter-based renal neuromodulation exhibits a relatively consistent impact on sympathetic nerve function and viability.

Example 4

Example 4 describes a method for treating human patients with renal denervation and anticipated outcomes of such treatment. In this example, human patients will be treated with renal denervation and a method of treatment includes modulating nerve tissue surrounding one or more primary branch trunks (e.g., one or more primary branch vessels distal to the primary bifurcation). In this example, modulating nerve tissue includes forming up to about four lesions (e.g., about 2 lesions to about 4 lesions) in the primary branch in the region spanning from about 5 mm distal to the primary bifurcation to about 5 mm proximal to the ureter or the kidney. Modulation of nerve tissue at branch treatment sites and/or different combinations of treatment sites within the renal vasculature can be performed using a multi-electrode Symplicity Spyral™ catheter, from Medtronic, Inc. Other multi-electrode, spiral/helical-shaped catheters for forming multiple lesions along the length of the vessel are contemplated for these methods. Systemic catecholamines and/or their subsequent degradation products could be measured in either plasma, serum or urine to serve as surrogate markers to measure procedural efficacy such as described in U.S. Provisional Patent Application No. 62/042,821, filed Aug. 28, 2014, and incorporated herein by reference in its entirety.

A method for efficaciously neuromodulating renal nerve tissue in a human patient can include assessing the diameter of the branch vessel to be treated. Renal artery branch vessels having a diameter greater than 3 mm (e.g., about 3 mm to about 8 mm in diameter) can be treated by advancing a multi-electrode Symplicity Spyral™ catheter (e.g., under fluoroscopic guidance) to the first renal artery branch vessel such that the proximal-most electrode is positioned approximately 5 mm distal to the bifurcation. In one procedure, if the distalmost electrode is not positioned within 5 mm of the ureter or the kidney, energy (e.g., RF energy) can be delivered by all electrodes along the catheter to form a spiral/helical-shaped lesion pattern. If the catheter does not achieve stable wall contact with the branch vessel wall, or if the first renal artery branch vessel is short and/or narrow and/or the distal-most portion of the branch vessel is not desirable for treatment, the distalmost electrode(s) can optionally and selectively be deselected for delivery of energy prior to ablation treatment.

In procedures where a branch tapers down to a diameter smaller than 3 mm and/or is not long enough to accommodate multiple electrodes (e.g., 4 electrodes), the catheter can be advanced to insert a fewer number of electrodes into the renal artery branch vessel such that the proximal portion (e.g., carrying the proximal-most electrodes) of the catheter can be positioned across the first bifurcation. Electrodes that are located at or near the primary bifurcation can be deselected by the operator (e.g., via the electrical control device, user interface, etc.) prior to ablation treatment. Energy (e.g., RF energy, etc.) will not be delivered to deselected electrodes when the energy generator is activated.

Following treatment at the first renal artery branch, the catheter can be withdrawn into the main renal vessel and then advanced under fluoroscopy into a second renal artery branch and the treatment procedure can be repeated. Some methods can include treating two branch vessels with different anatomical geometries (e.g., varying diameters, varying lengths, etc.), wherein an operator can select and deselect active electrode(s) along the multi-electrode Symplicity Spyral™ catheter depending on the positioning of the catheter within the different branches. Other methods can include treating greater than two or all of the primary branch vessels branching from the main renal vessel (e.g., distal to a primary bifurcation). As described above, these methods may also include combining neuromodulation of renal nerve tissue surrounding one or more primary branch vessels with neuromodulation of renal nerve tissue at one or more additional treatment locations (e.g., one or more locations along the main renal vessel).

It is anticipated that the positioning of the treatment device within the renal vasculature at a branch vessel and forming lesions in a spiral/helical-shaped or near spiral/helical-shaped pattern distal to the bifurcation (e.g., from about 5 mm distal to the primary bifurcation, from about 2-6 mm distal to the primary bifurcation, etc.) will result in increased efficacy of modulation of targeted nerves, as measured by levels of catecholamines and degradation products thereof in plasma, serum or urine pre- and post-procedure (described in above-referenced U.S. Provisional Patent Application No. 62/042,821).

ADDITIONAL EXAMPLES

1. A method, comprising:
   intravascularly advancing an elongate shaft of a catheter to renal vasculature of a human patient, the renal vasculature including—
      a main vessel directly connected to an aorta of the patient and extending distally toward a kidney, and a bifurcation at a distal end of the main vessel;
   locating a neuromodulation element of the catheter within a distalmost portion of the main vessel; and
   modulating nerve tissue within an anatomical region extending circumferentially around the distalmost portion of the main vessel via the neuromodulation element.

2. The method of example 1 wherein:
   the main vessel has a longitudinal axis extending from the aorta to the bifurcation;
   modulating nerve tissue within the anatomical region extending circumferentially around the distalmost portion of the main vessel includes using the neuromodulation element to form one or more lesions extending through a wall of the main vessel into the anatomical region extending circumferentially around the distalmost portion of the main vessel; and
   the one or more lesions collectively are—
      circumferentially continuous within the anatomical region along a plane perpendicular to a portion of the longitudinal axis extending through the distalmost portion of the main vessel, and
      circumferentially discontinuous at the wall of the main vessel along all planes perpendicular to the portion of the longitudinal axis extending through the distalmost portion of the main vessel.

3. The method of example 1 or example 2 wherein the main vessel is stented, and wherein locating a neuromodulation element of the catheter within a distalmost portion of the main vessel includes locating the neuromodulation element distal to a stent.

4. The method of example 1 or example 2 wherein modulating nerve tissue within the anatomical region extending circumferentially around the distalmost portion of the main vessel includes using the neuromodulation element to preferentially modulate nerve tissue within the anatomical region extending circumferentially around the distalmost portion of the main vessel relative to nerve tissue within an anatomical region extending circumferentially around a proximal-most portion of the main vessel and relative to nerve tissue within an anatomical region extending circumferentially around a middle portion of the main vessel between the proximal-most and distalmost portions of the main vessel.

5. The method of any one of examples 1-4 wherein:
   the catheter, the shaft, and the neuromodulation element are a first catheter, a first shaft, and a first neuromodulation element, respectively; and
   the method further comprises—
      withdrawing the first catheter from the patient,
      intravascularly advancing an elongate second shaft of a second catheter to the renal vasculature,
      locating a second neuromodulation element of the second catheter within a branch vessel of the renal vasculature distal to the bifurcation, and
      modulating nerve tissue within an anatomical region extending circumferentially around the branch vessel via the second neuromodulation element.

6. The method of example 5, further comprising measuring a degree of neuromodulation achieved using the first neuromodulation element to modulate nerve tissue within the anatomical region extending circumferentially around the distalmost portion of the main vessel, and wherein locating the second neuromodulation element and modulating nerve tissue within the anatomical region extending circumferentially around the branch vessel includes locating the second neuromodulation element and using the second neuromodulation element to modulate nerve tissue within the anatomical region extending circumferentially around the branch vessel in response to an insufficiency of the degree of neuromodulation.

7. The method of any one of examples 1-4 wherein:
   advancing the shaft includes advancing the shaft while the neuromodulation element is in a low-profile delivery state; and
   the method further comprises transforming the neuromodulation element between the low-profile delivery state and an expanded treatment state after locating the neuromodulation element within the distalmost portion of the main vessel and before modulating nerve tissue within the anatomical region extending circumferentially around the distalmost portion of the main vessel.

8. The method of example 7 wherein:
   the neuromodulation element includes a balloon; and
   transforming the neuromodulation element includes inflating the balloon.

9. The method of example 7 wherein:
   the neuromodulation element includes an elongate support structure carrying a plurality of electrodes, the support structure having a helical form when unconstrained;
   advancing the shaft includes advancing the shaft while the support structure is constrained; and
   transforming the neuromodulation element includes reducing constraint on the support structure such that the support structure moves toward having the helical form.

10. The method of example 7 wherein:
    the neuromodulation element includes an elongate electrode having a helical form when unconstrained;
    advancing the shaft includes advancing the shaft while the electrode is constrained; and
    transforming the neuromodulation element includes reducing constraint on the electrode such that the electrode moves toward having the helical form.

11. The method of any one of examples 1-4 wherein:
    the neuromodulation element is a first neuromodulation element; and
    the method further comprises—
       locating a second neuromodulation element of the catheter within a branch vessel of the renal vasculature distal to the bifurcation, and
       modulating nerve tissue within an anatomical region extending circumferentially around the branch vessel after locating the second neuromodulation element.

12. The method of example 11 wherein:
    advancing the shaft includes advancing the shaft while the second neuromodulation element is in a low-profile delivery state; and
    the method further comprises transforming the second neuromodulation element between the low-profile delivery state and an expanded treatment state after locating the second neuromodulation element and modulating nerve tissue within the anatomical region extending circumferentially around the branch vessel.

13. The method of example 11 wherein:
the second neuromodulation element includes a balloon; and
transforming the second neuromodulation element includes inflating the balloon.

14. The method of example 11 wherein:
the second neuromodulation element includes an elongate support structure carrying a plurality of electrodes, the support structure having a helical form when unconstrained;
advancing the shaft includes advancing the shaft while the support structure is constrained; and
transforming the second neuromodulation element includes reducing constraint on the support structure such that the support structure moves toward having the helical form.

15. The method of example 11 wherein:
the second neuromodulation element includes an elongate electrode having a helical form when unconstrained;
advancing the shaft includes advancing the shaft while the electrode is constrained; and
deploying the second neuromodulation element includes reducing constraint on the electrode such that the electrode moves toward having the helical form.

16. The method of any one of examples 11-15, further comprising measuring a degree of neuromodulation achieved using the first neuromodulation element to modulate nerve tissue within the anatomical region extending circumferentially around the distalmost portion of the main vessel, wherein locating the second neuromodulation element and modulating nerve tissue within the anatomical region extending circumferentially around the branch vessel includes locating the second neuromodulation element and modulating nerve tissue within the anatomical region extending circumferentially around the branch vessel in response to an insufficiency of the degree of neuromodulation.

17. A method, comprising:
intravascularly advancing an elongate shaft of a catheter to renal vasculature of a human patient, the renal vasculature including—
a main vessel directly connected to an aorta of the patient and extending distally toward a kidney,
a bifurcation at a distal end of the main vessel, and
a branch vessel distal to the bifurcation;
modulating nerve tissue within an anatomical region extending circumferentially around the main vessel;
measuring a degree of neuromodulation achieved by modulating nerve tissue within the anatomical region extending circumferentially around the main vessel; and
in response to an insufficiency of the degree of neuromodulation, modulating nerve tissue within an anatomical region extending circumferentially around the branch vessel.

18. The method of example 17 wherein the main vessel is stented.

19. The method of example 17 or example 18 wherein:
the degree of neuromodulation is a first degree of neuromodulation;
the branch vessel is a first branch vessel;
the renal vasculature includes a second branch vessel, the first and second branch vessels being independently connected to the main vessel; and
the method further comprises—
measuring a second degree of neuromodulation after modulating nerve tissue within the anatomical region extending circumferentially around the first branch vessel; and
in response to an insufficiency of the second degree of neuromodulation, modulating nerve tissue within an anatomical region extending circumferentially around the second branch vessel.

20. The method of example 19 wherein:
the renal vasculature includes a third branch vessel, the first, second, and third branch vessels being independently connected to the main vessel; and
the method further comprises—
measuring a third degree of neuromodulation after modulating nerve tissue within the anatomical region extending circumferentially around the second branch vessel; and
in response to an insufficiency of the third degree of neuromodulation, modulating nerve tissue within an anatomical region extending circumferentially around the third branch vessel.

21. A method including any non-conflicting combination of the preceding examples 1-20.

22. A method, comprising:
intravascularly positioning a neuromodulation element of a catheter within renal vasculature of a human patient, the renal vasculature including—
a main vessel directly connected to an aorta of the patient and extending distally toward a kidney,
a bifurcation at a distal end of the main vessel, and
a branch vessel distal to the bifurcation; modulating nerve tissue within an anatomical region extending circumferentially around
the branch vessel; and
modulating nerve tissue within an anatomical region extending circumferentially around the main vessel.

23. The method of example 22 wherein the branch vessel is a first branch vessel, and wherein the method further comprises modulating nerve tissue within an anatomical region extending circumferentially around a second branch vessel, the second branch vessel distal to the bifurcation.

24. The method of example 23 wherein the second branch vessel is modulated before the main vessel is modulated.

25. The method of any one of examples 22-24 wherein modulating nerve tissue within an anatomical region extending circumferentially around the main vessel includes using the neuromodulation element to preferentially modulate nerve tissue within the anatomical region extending circumferentially around the distalmost portion of the main vessel relative to nerve tissue within an anatomical region extending circumferentially around a proximal-most portion of the main vessel and relative to nerve tissue within an anatomical region extending circumferentially around a middle portion of the main vessel between the proximal-most and distalmost portions of the main vessel.

26. The method of any one of examples 22-24 wherein modulating nerve tissue within an anatomical region extending circumferentially around the main vessel includes using the neuromodulation element to preferentially modulate nerve tissue within the anatomical region extending circumferentially around the distalmost third of the main vessel.

27. The method of any one of examples 22-26 wherein modulating nerve tissue within an anatomical region extending circumferentially around the branch vessel includes using the neuromodulation element to form between two and four lesions extending through a wall of the main vessel into the anatomical region extending circumferentially around the branch vessel.

28. The method of any one of examples 22-27 wherein modulating nerve tissue within an anatomical region extending circumferentially around the branch vessel includes modulating nerve tissue with a first power level, and wherein modulating nerve tissue within an anatomical region extending circumferentially around the main vessel includes modulating nerve tissue with a second power level greater than the first power level.

29. The method of any one of examples 22-28 wherein:
the neuromodulation element includes an elongate support structure carrying a plurality of electrodes, the support structure having a helical form when unconstrained;
positioning the neuromodulation element includes positioning the neuromodulation element such that a proximal-most electrode is distal to the bifurcation when unconstrained; and
wherein the method further includes deselecting one or more distal electrode(s) on the elongate support structure prior to modulating the nerve tissue.

30. The method of any one of examples 22-28 wherein:
the neuromodulation element includes an elongate support structure carrying a plurality of electrodes, the support structure having a helical form when unconstrained;
positioning the neuromodulation element includes positioning the neuromodulation element such that the support structure is positioned across the bifurcation when unconstrained; and
wherein the method further includes deselecting one or more proximal electrode(s) on the elongate support structure prior to modulating the nerve tissue.

31. The method of any one of examples 22-30 wherein the method reduces sympathetic neural activity in the human patient.

32. The method of any one of examples 22-30 wherein the method reduces norepinephrine spillover in the human patient.

33. A method for treating a human patient diagnosed with a measurable physiological parameter associated with systemic sympathetic overactivity or hyperactivity, comprising:
neuromodulating renal nerve tissue within an anatomical region extending circumferentially around a branch renal vessel, wherein the branch renal vessel is located distal to a bifurcation in a main renal artery of the human patient;
neuromodulating renal nerve tissue within an anatomical region extending circumferentially around the main renal artery of the human patient; and
wherein the method reduces sympathetic neural activity in the human patient.

34. The method of example 33 wherein the measurable physiological parameter is elevated blood pressure.

35. The method of example 33 or example 34 wherein the human patient is hypertensive.

36. The method of any one of examples 33-35 wherein the method reduces norepinephrine spillover in the human patient.

37. A device configured to perform any of the methods of the preceding examples 1-36.

38. A device for performing renal neuromodulation, comprising:
a catheter having an elongate shaft, the catheter comprising a first neuromodulation element operably connected to the shaft, and a second neuromodulation element,
wherein the first neuromodulation element is configured to be located within a distalmost portion of a main renal artery connected to an aorta of the patient and extending distally toward a kidney, and
wherein the second neuromodulation element is configured to be located within a branch vessel of the renal artery distal to a bifurcation at a distal end of the main renal artery.

39. The device of example 38, wherein the first neuromodulation element includes an elongate support structure having a plurality of longitudinally spaced-apart electrodes.

40. The device of example 39, wherein the elongate support structure has a helical or spiral form when unconstrained.

41. The device of example 39 or 40, wherein the catheter is configured to be delivered over a guidewire and wherein the support structure is configured to assume a preformed helical or spiral configuration when the guidewire is retracted.

42. The device of any of the preceding examples, wherein the device further comprises a sheath and wherein the catheter assumes a helical or spiral configuration when pushed or otherwise presented distally from the sheath.

43. The device of any of the preceding examples, wherein the second neuromodulation element is operably connected to the shaft and/or to the first neuromodulation element.

44. The device of any of the preceding examples, wherein the second neuromodulation element includes an elongate conduit connected to a distal end of the support structure.

45. The device of any of examples 38 to 44, wherein the second neuromodulation element includes at least one wire electrode.

46. The device of example 45, wherein the at least one wire electrode has a low-profile delivery state and a helical or a spiral form when unconstrained.

47. The device of example 45 or 46, wherein the at least one wire electrode has a low-profile delivery state when constrained within the elongate conduit.

48. The device of any of examples 45 to 47, wherein the second neuromodulation element includes multiple wire electrodes which can be individually guided into respective branch vessels.

49. The device of any of examples 38 to 44, wherein the second neuromodulation element includes an elongate support and electrodes.

50. The device of any of examples 38 to 44, wherein the second neuromodulation element has a single element tapering distally.

51. The device of example 50, wherein the first and second neuromodulation elements are continuous.

52. The device of example 51, wherein the device is configured so that a distal portion of a single elongate support element can be deployed within one of the branch vessels while a proximal portion of the single elongate support element is deployed within the distal portion of a main vessel.

53. The device of example 51, wherein the second neuromodulation element includes a balloon.

54. The device according to example 51, wherein the first neuromodulation element includes a balloon.

55. The device of any of examples 38 to 54, wherein the device is configured such that the proximal-most lesion is at least about 5 mm distal to a bifurcation of the main renal vessel.

56. The device of any of examples 38 to 55, wherein the device is configured such that the proximal-most electrodes is distal to the primary bifurcation, preferably about 2 to about 6 mm distal to the primary bifurcation.

57. The device of any of examples 39 to 56, wherein the device is configured such that one or more electrodes of the elongate support structure may be deselected such that only the selected electrodes deliver energy.

58. A system for performing renal neuromodulation, comprising
a device of any of the preceding claims, and
a console configured to control, monitor, supply energy to, and/or otherwise support operation of the catheter.

59. A system for performing renal neuromodulation, comprising
a catheter having an elongate shaft, the catheter comprising a first neuromodulation element operably connected to the shaft, wherein the first neuromodulation element includes an elongate support structure having a plurality of longitudinally spaced-apart electrodes, and
a console configured to control, monitor, supply energy to, and/or otherwise support operation of the catheter.

60. The system of example 58 or 59, wherein the system is configured to individually supply different and/or varying amounts of energy to electrodes based on an electrode's location along the vasculature when deployed.

61. The system of any of examples 58 to 60, wherein the system is configured such that an electrode positioned along the proximal portion of a main vessel imparts higher power than an electrode positioned along a distalmost portion of the main vessel and/or a branch vessel.

62. The system of any of examples 58 to 61, wherein the system is further configured such that the duration of power delivery can vary depending on the position of one or more electrodes along the vasculature.

63. The system of any of examples 58 to 62, wherein the system is further configured such that that an electrode positioned along the proximal portion of a main vessel imparts power for a longer duration than an electrode positioned along a distalmost portion of the main vessel and/or a branch vessel.

64. A method for controlling therapeutic energy delivery to a multi-electrode neuromodulation element positioned in a renal vessel during a neuromodulation treatment, the method comprising
individually supplying different and/or varying amounts of energy to the electrodes based on an electrode's location along the vasculature.

65. The method of example 64, further comprising
imparting higher power to an electrode positioned along the proximal portion of a main vessel than to an electrode positioned along a distalmost portion of the main vessel and/or a branch vessel.

66. The method of example 64 or 65, further comprising
varying the duration of power delivery depending on the position of one or more electrodes along the vasculature.

67. The method of any of examples 64 to 66, further comprising
imparting power to an electrode positioned along the proximal portion of a main vessel for a longer duration than to an electrode positioned along a distalmost portion of the main vessel and/or a branch vessel.

68. A method, comprising:
intravascularly advancing an elongate shaft of a catheter to renal vasculature of a human patient;
locating a first neuromodulation element of the catheter within a distalmost portion of a main renal artery directly connected to an aorta of the patient and extending distally toward a kidney of the patient;
locating a second neuromodulation element of the catheter within a branch vessel of the renal artery distal to a bifurcation at a distal end of the main renal artery;
modulating nerve tissue within an anatomical region extending about the distalmost portion of the main renal artery via the first neuromodulation element; and
modulating nerve tissue within an anatomical region extending about the branch vessel via the second neuromodulation element.

69. The method of example 68 wherein intravascularly advancing an elongate shaft of a catheter to renal vasculature comprises delivering the catheter over a guidewire, and wherein the first neuromodulation element assumes a preformed spiral/helical configuration within the distalmost portion of the main renal artery when the guidewire is retracted.

70. The method of example 68 wherein intravascularly advancing an elongate shaft of a catheter to renal vasculature comprises delivering the catheter within a sheath, and wherein the first neuromodulation element assumes a preformed spiral/helical configuration within the distalmost portion of the main renal artery when removed from the sheath.

71. The method of example 68 wherein the second neuromodulation element is operably connected to the shaft.

72. The method of example 68 wherein the second neuromodulation element is operably connected to the first neuromodulation element.

73. The method of example 68 wherein the second neuromodulation element comprises at least one wire electrode, and wherein locating the second neuromodulation element of the catheter within the branch vessel comprises delivering the second neuromodulation element to the branch vessel in a low-profile state and transforming the second neuromodulation element to an unconstrained spiral/helical state within the branch vessel.

74. The method of example 68 wherein the second neuromodulation element comprises multiple wire electrodes, and wherein locating the second neuromodulation element of the catheter within the branch vessel comprises locating a first wire electrode within a first branch vessel and a second wire electrode within a second, different branch vessel.

75. The method of example 68 wherein the first and second neuromodulation elements are a single continuous elongate element, and wherein:
locating a first neuromodulation element of the catheter within a distalmost portion of a main renal artery comprises locating a proximal portion of the single elongate element within the distalmost portion of the main renal artery; and
locating a second neuromodulation element of the catheter within a branch vessel comprises locating a distal portion of the single elongate element within the branch vessel.

76. The method of example 68 wherein the first neuromodulation element further comprises a balloon, and wherein locating the first neuromodulation element of the catheter within the distalmost portion of the main renal artery comprises inflating the balloon before modulating nerve tissue via the first neuromodulation element.

77. The method of example 68 wherein the second neuromodulation element further comprises a balloon, and wherein locating the second neuromodulation element of the catheter within the branch vessel comprises inflating the balloon before modulating nerve tissue via the second neuromodulation element.

78. The method of any one of examples 68 to 77 wherein modulating nerve tissue via the second neuromodulation element comprises forming a plurality of lesions, and wherein the proximalmost lesion is at least about 5 mm distal to the bifurcation of the main renal artery.

79. The method of any one of examples 68 to 77 wherein modulating nerve tissue via the first neuromodulation element comprises forming a plurality of lesions, and wherein the proximalmost lesion is at least about 2 mm to 6 mm distal to the bifurcation of the main renal artery.

80. The method of any one of examples 68 to 79 wherein the branch vessel is modulated before the main renal artery is modulated.

81. The method of any one of examples 68 to 79 wherein the main renal artery is modulated before the branch vessel is modulated.

82. The method of any one of examples 68 to 79 wherein the main renal artery and the branch vessel are modulated simultaneously.

83. A method, comprising:
intravascularly advancing an elongate shaft of a catheter to renal vasculature of a human patient;
locating a neuromodulation element of the catheter within a distalmost portion of a main vessel directly connected to an aorta of the patient and extending distally toward a kidney, wherein the neuromodulation element includes an elongate support structure having a plurality of longitudinally spaced-apart electrodes; and
ablating nerve tissue within an anatomical region extending circumferentially around the distalmost portion of the main vessel via the electrodes of the neuromodulation element.

84. The method of example 83 wherein:
the main vessel has a longitudinal axis extending from the aorta to a bifurcation at a distal end of the main renal artery;
ablating nerve tissue within the anatomical region extending circumferentially around the distalmost portion of the main vessel includes using the neuromodulation element to form one or more lesions extending through a wall of the main vessel into the anatomical region extending circumferentially around the distalmost portion of the main vessel; and
the one or more lesions collectively are—
circumferentially continuous within the anatomical region along a plane perpendicular to a portion of the longitudinal axis extending through the distalmost portion of the main vessel, and
circumferentially discontinuous at the wall of the main vessel along all planes perpendicular to the portion of the longitudinal axis extending through the distalmost portion of the main vessel.

85. The method of example 83 or 84 wherein the main vessel is stented, and wherein locating a neuromodulation element of the catheter within a distalmost portion of the main vessel includes locating the neuromodulation element distal to a stent.

86. The method of example 83 wherein:
the catheter, the shaft, and the neuromodulation element are a first catheter, a first shaft, and a first neuromodulation element, respectively; and
the method further comprises—
withdrawing the first catheter from the patient;
intravascularly advancing an elongate second shaft of a second catheter to the renal vasculature;
locating a second neuromodulation element of the second catheter within a branch vessel of the renal vasculature distal to the bifurcation;
ablating nerve tissue within an anatomical region extending circumferentially around the branch vessel via the second neuromodulation element; and
withdrawing the second catheter from the patient.

87. The method of example 86, further comprising measuring a degree of neuromodulation achieved using the first neuromodulation element to modulate nerve tissue within the anatomical region extending circumferentially around the distalmost portion of the main vessel, and wherein locating the second neuromodulation element and ablating nerve tissue within the anatomical region extending circumferentially around the branch vessel includes locating the second neuromodulation element and using the second neuromodulation element to modulate nerve tissue within the anatomical region extending circumferentially around the branch vessel in response to an insufficiency of the degree of neuromodulation.

88. The method of example 86 wherein ablating nerve tissue within an anatomical region extending circumferentially around the branch vessel includes modulating nerve tissue with a first power level, and wherein modulating nerve tissue within an anatomical region extending circumferentially around the main vessel includes modulating nerve tissue with a second power level greater than the first power level.

89. The method of example 83 wherein:
advancing the shaft includes advancing the shaft while the neuromodulation element is in a low-profile delivery state; and
the method further comprises transforming the neuromodulation element between the low-profile delivery state and an expanded treatment state after locating the neuromodulation element within the distalmost portion of the main vessel and before ablating nerve tissue within the anatomical region extending circumferentially around the distalmost portion of the main vessel, wherein, in the extended treatment state, the neuromodulation element has a helical form.

90. A method for treating a human patient diagnosed with a measurable physiological parameter associated with systemic sympathetic overactivity or hyperactivity, the method comprising:
ablating renal nerves within an anatomical region extending about a branch renal vessel of the patient, wherein the branch renal vessel is located distal to a bifurcation in a main renal artery of the patient; and
ablating renal nerves within an anatomical region extending circumferentially around the main renal artery of the patient,
wherein ablating the renal nerves results in a decrease in renal sympathetic neural activity in the patient.

91. The method of example 90 wherein ablating the renal nerves results in a therapeutically beneficial reduction in clinical symptoms of hypertension in the patient.

92. The method of example 90 or 91 wherein ablating the renal nerves comprises systemically reducing sympathetic tone in the patient.

93. The method of any of examples 90 to 92 wherein ablating the renal nerves reduces norepinephrine spillover in the patient.

Conclusion

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments may also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

The methods disclosed herein include and encompass, in addition to methods of practicing the present technology (e.g., methods of making and using the disclosed devices and systems), methods of instructing others to practice the present technology. For example, a method in accordance with a particular embodiment includes intravascularly advancing an elongate shaft of a catheter to renal vasculature of a human patient, locating a neuromodulation element of the catheter within a distalmost portion of a main vessel of the renal vasculature, and modulating nerve tissue within an anatomical region extending circumferentially around the distalmost portion of the main vessel via the neuromodulation element. A method in accordance with another embodiment includes instructing such a method.

The headings provided herein are for convenience only and should not be construed as limiting the subject matter disclosed. As used herein, the terms "distal" and "proximal" define a position or direction with respect to a clinician or a clinician's control device (e.g., a handle of a catheter). The terms "distal" and "distally" refer to a position distant from or in a direction away from a clinician or a clinician's control device. The terms "proximal" and "proximally" refer to a position near or in a direction toward a clinician or a clinician's control device. Within an un-catheterized renal artery, the terms "distal" and "distally" refer to a position distant from or in a direction away from the renal artery ostium. The terms "proximal" and "proximally" refer to a position near or in a direction toward the renal artery ostium. Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation.

Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments of the present technology.

We claim:

1. A method, comprising:
intravascularly advancing an elongate shaft of a catheter within renal vasculature of a patient, the catheter comprising a neuromodulation element comprising a plurality of electrodes;
executing a first modulating step using the neuromodulation element, the first modulating step comprising modulating first nerve tissue with a first neuromodulation energy level within an anatomical region extending about a main renal artery directly connected to an aorta of the patient and extending distally toward a kidney of the patient, wherein the first modulating step comprises forming a plurality of lesions within the anatomical region extending about the main renal artery;
executing a second modulating step using the neuromodulation element, the second modulating step comprising modulating second nerve tissue with a second neuromodulation energy level within an anatomical region extending about a branch vessel of the main renal artery, wherein the second nerve tissue excludes nerve fibers that diverge at least partially toward a non-renal destination, the first neuromodulation energy level being higher than the second neuromodulation energy level; and
repositioning the neuromodulation element within the renal vasculature between the first modulating step and the second modulating step such that the first modulating step and the second modulating step are sequentially executed in either order,
wherein the first neuromodulation energy level is delivered for a longer duration than the second neuromodulation energy level.

2. The method of claim 1, wherein the second nerve tissue excludes nerve fibers that do not terminate within the kidney.

3. The method of claim 1, wherein the intravascularly advancing comprises the repositioning, and wherein the neuromodulation element is in a low-profile state for each of the intravascularly advancing and repositioning.

4. The method of claim 1, wherein the neuromodulation element is in a first expanded, deployed configuration for the first modulating step and in a second expanded, deployed configuration for the second modulating step,
wherein, in the first expanded, deployed configuration, the neuromodulation element contacts a wall of the main renal artery during the first modulating step, and
wherein, in the second expanded, deployed configuration, the neuromodulation element contacts a wall of the branch vessel during the second modulating step.

5. The method of claim 1 wherein the intravascularly advancing comprises delivering the catheter over a guidewire to the main renal artery for execution of the first modulating step, and wherein the neuromodulation element assumes a preformed spiral or helical configuration within a distalmost portion of the main renal artery when the guidewire is retracted for execution of the first modulating step.

6. The method of claim 1 wherein the intravascularly advancing comprises delivering the catheter within a sheath to the main renal artery for execution of the first modulating step, and wherein the neuromodulation element assumes a preformed spiral or helical configuration within a distalmost portion of the main renal artery when removed from the sheath for execution of the first modulating step.

7. The method of claim 1 wherein the first modulating step is executed before the second modulating step.

8. The method of claim 1 wherein the second modulating step is executed before the first modulating step.

9. The method of claim 1 wherein the intravascularly advancing comprises delivering the neuromodulation element to the branch vessel in the low-profile state, and thereafter transforming the neuromodulation element to an unconstrained spiral or helical state within the branch vessel.

10. The method of claim 1 wherein the neuromodulation element is a single continuous elongate element, and wherein:
intravascularly advancing comprises locating the neuromodulation element within a distalmost portion of the main renal artery for execution of the first modulating step and which in turn comprises locating a proximal portion of the single elongate element within the distalmost portion of the main renal artery; and
intravascularly advancing comprises locating the neuromodulation element within the branch vessel for execution of the second modulating step and which in turn comprises locating a distal portion of the single elongate element within the branch vessel.

11. The method of claim 1 wherein the second modulating step comprises forming a plurality of lesions, and wherein a proximal-most lesion of the plurality of lesions in the branch vessel is at least about 5 millimeters (mm) distal to a bifurcation of the main renal artery.

12. The method of claim 1 wherein the second modulating step comprises forming a plurality of lesions, and wherein the proximal-most lesion of the plurality of lesions within the branch vessel is at least about 1 mm distal to the bifurcation of the main renal artery.

13. The method of claim 1 wherein the first modulating step comprises forming a plurality of lesions, and wherein a distalmost lesion of the plurality of lesions is approximately 1 mm to 6 mm proximal to a bifurcation of the main renal artery.

14. The method of claim 1 wherein the branch vessel is modulated before the main renal artery is modulated, and wherein the repositioning comprises moving the neuromodulation element in a proximal direction after termination of the second modulating step and for a subsequent execution of the first modulating step.

15. The method of claim 1 wherein the main renal artery is modulated before the branch vessel is modulated, wherein the repositioning comprises moving the neuromodulation element in a distal direction after termination of the first modulating step and for a subsequent execution of the second modulating step.

16. The method of claim 1 wherein the branch vessel is a first branch vessel, and wherein the method further comprises:
retracting the neuromodulation element from the first branch vessel;
locating the neuromodulation element of the catheter within a second branch vessel of the main renal artery distal to a bifurcation of the main renal artery; and
executing a third modulating step comprising modulating third nerve tissue within an anatomical region extending about the second branch vessel via the neuromodulation element.

17. The method of claim 1, wherein the neuromodulation element comprises an elongate support structure, and wherein the plurality of electrodes are spaced along a length of the elongate support structure.

18. The method of claim 17, wherein the elongate support structure is configured to transform from a low profile delivery configuration to an expanded, deployed configuration in which the elongate support structure defines a helical or a spiral form.

19. The method of claim 1, wherein during the second modulating step, the neuromodulation element is disposed within the branch vessel such that a proximal-most electrode of the plurality of electrodes is distal to a primary bifurcation of the main renal artery.

20. A method, comprising:
intravascularly advancing an elongate shaft of a catheter within renal vasculature of a patient, the catheter comprising a neuromodulation element comprising a plurality of electrodes;
modulating first nerve tissue within an anatomical region extending about a main renal artery by at least delivering energy with a first neuromodulation energy level to at least one electrode of the plurality of electrodes;
modulating second nerve tissue within an anatomical region extending about a branch vessel of the main renal artery with a second neuromodulation energy level, wherein the second nerve tissue excludes nerve fibers that do not terminate within the kidney, the first neuromodulation energy level being higher than the second neuromodulation energy level; and
repositioning the neuromodulation element within the renal vasculature between the first modulating step and the second modulating step such that the first modulating step and the second modulating step are sequentially executed in either order,
wherein the first neuromodulation energy level is delivered for a longer duration than the second neuromodulation energy level.

* * * * *